United States Patent [19]
Amano et al.

[11] Patent Number: 5,730,137
[45] Date of Patent: Mar. 24, 1998

[54] MEDICATION DELIVERY CONTROL AND PULSE WAVE DETECTION APPARATUS

[75] Inventors: Kazuhiko Amano, Suwa; Kazuo Kodama, Yokohama; Hitoshi Ishiyama, Toride, all of Japan

[73] Assignee: Seiko Epson Corporation, Tokyo, Japan

[21] Appl. No.: 343,301

[22] Filed: Nov. 22, 1994

[30] Foreign Application Priority Data

Nov. 30, 1993 [JP] Japan ................................. 5-300548

[51] Int. Cl.⁶ ........................................................ A61B 5/00
[52] U.S. Cl. ........................ 128/672; 128/687; 128/690; 604/66
[58] Field of Search .............................. 128/672, 677, 128/680–3, 687, 690; 604/50, 65–67

[56] References Cited

U.S. PATENT DOCUMENTS

| | | | |
|---|---|---|---|
| 4,080,966 | 3/1978 | McNally et al. | 128/672 |
| 4,245,648 | 1/1981 | Trimmer et al. | 128/680 |
| 4,425,920 | 1/1984 | Bourland et al. | 128/672 |
| 4,710,164 | 12/1987 | Levin et al. | 604/66 |
| 5,269,301 | 12/1993 | Cohen | 604/66 |
| 5,381,797 | 1/1995 | Pak et al. | 128/687 |

FOREIGN PATENT DOCUMENTS

| | | |
|---|---|---|
| 0 183 351 | 6/1986 | European Pat. Off. . |
| 0 240 735 | 10/1987 | European Pat. Off. . |
| 0 408 483 | 1/1991 | European Pat. Off. . |

OTHER PUBLICATIONS

Proceedings Of The Annual International Conference Of The IEEE/EMBS, vol. 13, 3 Nov. 1991, Orlando ((US) pp. 2162–2163, .XP347338, N. Nishiura et al. "An Optical Telemetry Drug Injection Control and ECG System For Awake Animal Studies".

Primary Examiner—Robert L. Nasser
Attorney, Agent, or Firm—Mark P. Watson

[57] ABSTRACT

A microcomputer performs a frequency analysis of pulse waves which are taken at regular time intervals from a patient through a pulse wave detection section. Then, if the amplitudes and phases of the spectra of the pulse waves fulfill some set conditions, either $\alpha$-blocker or $\beta$-blocker is given to the patient, and the patient's circulatory activity is maintained in a stable condition.

9 Claims, 15 Drawing Sheets

| PEAK DATA | PEAK ADDRESS | ADR3 | 0 | 1 | 2 | 3 | 4 |
|---|---|---|---|---|---|---|---|
| | WAVEFORM VALUE ADDRESS | ADR1 | | | | | |
| | PEAK TYPE | B/T | | | | | |
| | WAVEFORM VALUE | W | | | | | |
| | STROKE | STRK | | | | | |
| | SLOPE DATA | SLP | | | | | |

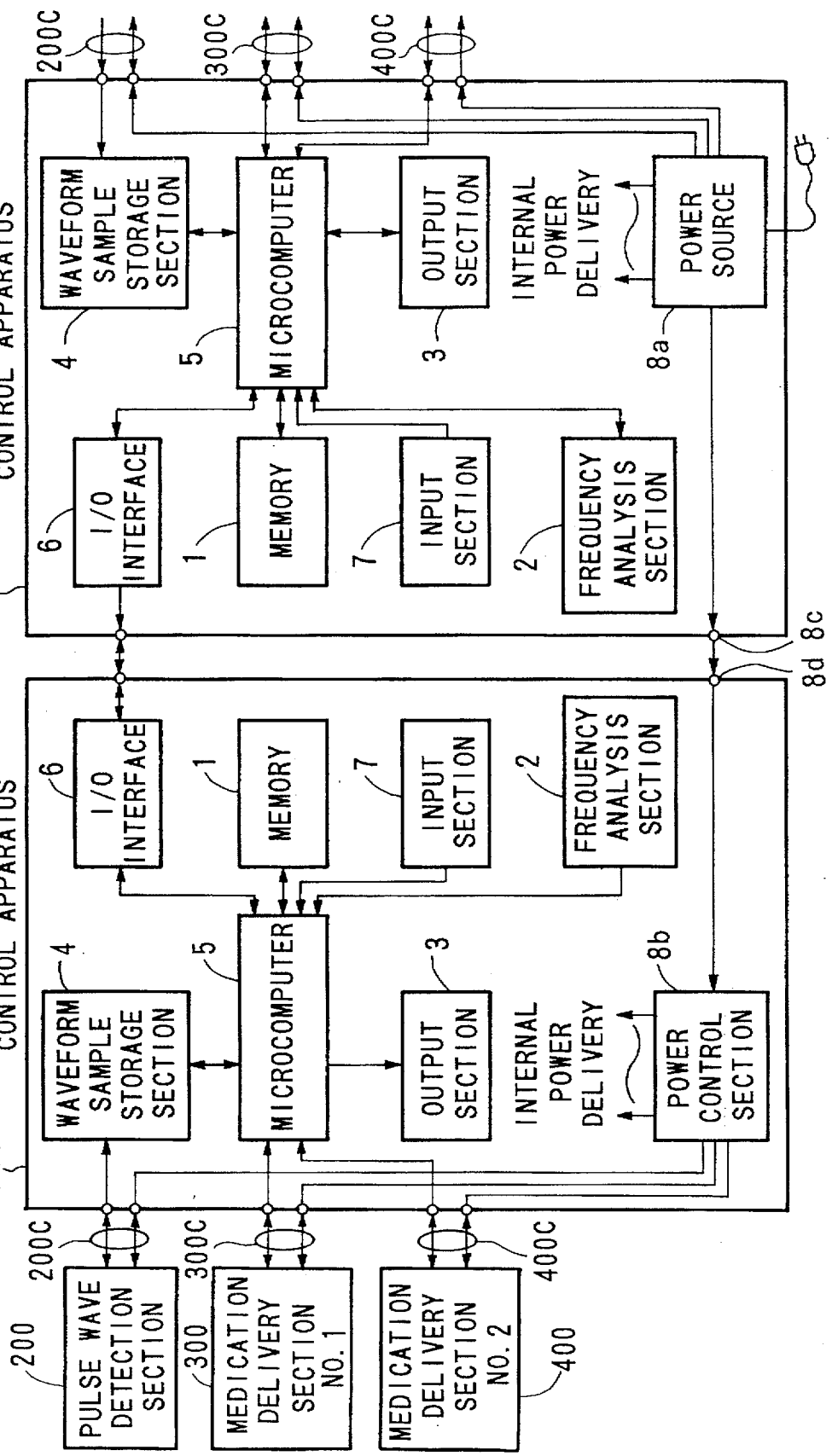

5,730,137

MEDICATION DELIVERY CONTROL AND PULSE WAVE DETECTION APPARATUS

BACKGROUND OF THE INVENTION

1. Field of the Invention

The present invention relates to a medication delivery control apparatus used in the control of the delivery of medication and a pulse wave detection apparatus used in the determination of the necessity of the delivery of medication.

2. Background Art

For patients who suffer from such ailments of the circulatory system as hypertension and heart failure, because the action of their circulatory flow is often unstable, it is necessary to continually watch their condition and prevent the occurrence of any dangerous situations. In this case, agents for the control of the behavior of the circulatory system, such agents as α-blocker, β-blocker, Ca antagonist, and ACE inhibitor are known. Therefore, a procedure is required to control the condition of the circulatory system by delivering circulatory drugs such as α-blocker, β-blocker, Ca antagonist, and ACE inhibitor to the patient and stabilizing the action of the patient's circulatory flow.

However, because the delivery of circulatory drugs as discussed above requires a timely reaction in case the patient's condition deviates from normal, the constant observation of the patient's condition by a doctor is necessary and it therefore requires a lot of labor. Furthermore, patients with extreme symptoms must receive circulatory drugs so often as to be able to refer to it as constant, and in order to receive the medication they must remain lying down on a hospital bed.

SUMMARY OF THE INVENTION

The present invention takes consideration of the situation discussed above, and has as its objective the presentation of a medication delivery apparatus which has the ability to perform the medication delivery necessary based on the results of the observation of the patient's condition.

In order to reach this objective, the present invention has a pulse wave detection means for receiving pulse waves from the patient at regular time intervals, a pulse wave analysis means for determining the waveform parameters of the said pulse wave, and a medication delivery control means for ordering the delivery of medication in the event that said waveform parameters fulfill some set conditions.

Then, the pulse wave received from the pulse wave detection means is analyzed by the waveform analysis means, and the waveform parameters are thus determined. Next, the medication control means investigates whether or not the waveform parameters fulfill the set conditions, and if they do then a medication delivery order is output.

Due to this kind of composition and function, it is possible to perform automatically the delivery of the medication at a time when the patient truly needs it.

Furthermore, another objective of this invention is to present a pulse wave detection apparatus which can detect the features of the pulse waves of the patient.

In order to reach this objective, the present invention has a pulse wave detection means for detecting the pulse waves from the patient, and a pulse wave analysis means for determining the waveform parameters of the pulse waves. Then, the features of the patient's pulse waves are determined based on the waveform parameters of the pulse waves.

Due to the utilization of this pulse wave detection apparatus, it is possible to determine the necessity for medication delivery.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 19 is a block diagram showing the composition of the medication delivery apparatus according to the second embodiment of the present invention;

DESCRIPTION OF THE PREFERRED EMBODIMENTS

The embodiments of the medication delivery control apparatus pertaining to the present invention are explained below with reference to the drawings.

The First Embodiment

The medication delivery control apparatus according to the present embodiment is used in order to maintain a patient's blood pressure in a stable condition. It determines whether or not the patient is in a condition requiring medication, and depending upon this determination it provides the patient with the necessary circulatory medication such as α-blocker or β-blocker. The circulatory medication mentioned here includes drugs or hormones which directly or indirectly affect the circulatory system.

A. Prior Examination

In designing the apparatus pertaining to the present embodiment, it is necessary to determine the conditions under which the patient requires medication. Upon repeated medication delivery experiments, the inventors of the present invention observed that, "the activity of the sympathetic nerve receptors such as α-receptors and β-receptors which govern the behavior of the circulatory system of hypertension patients appears as changes in their pulse wave."

Figure 1:
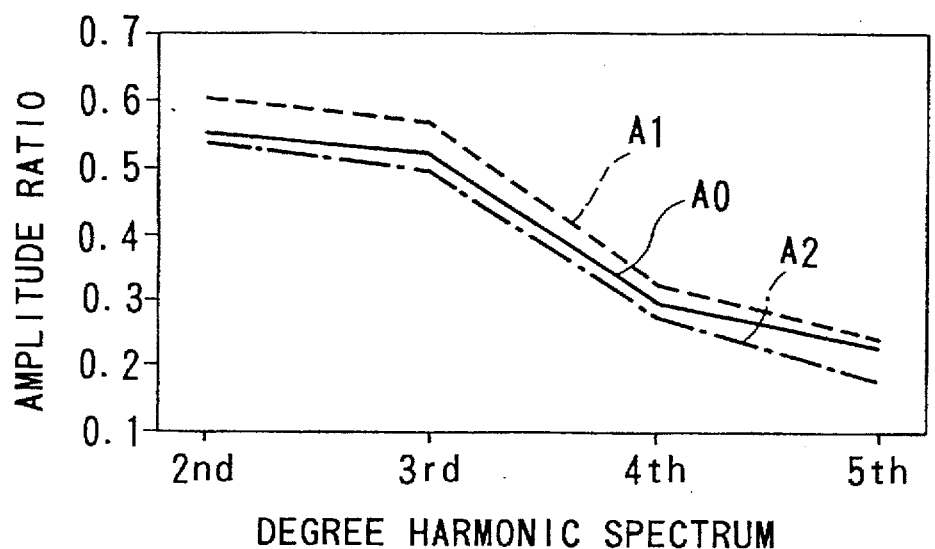
FIG. 1 shows a diagram demonstrating the change in the amplitudes of the pulse wave spectra due to the delivery of circulatory drugs.
Figure 2:
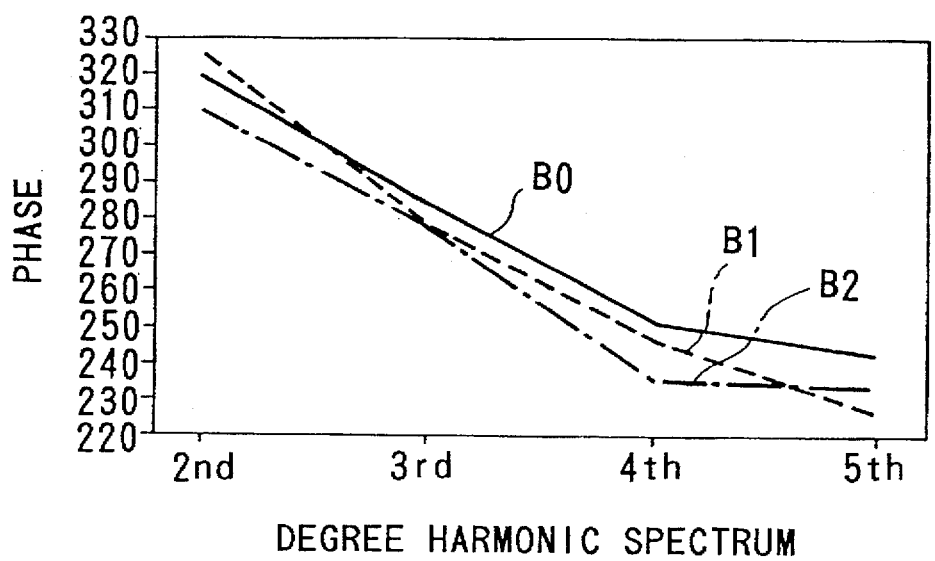
FIG. 2 shows a diagram demonstrating the change in the phases of the pulse wave spectra due to the delivery of circulatory drugs.

FIGS. 1 and 2 show the changes in the pulse spectrum after the circulatory medication is given. Specifically, in FIG. 1 the graphs A0, A1, and A2 show the amplitude ratio between the fundamental wave spectrum and each harmonic wave spectrum of the pulse waves, with graph A0 showing the normal amplitude ratio, graph A1 showing the amplitude ratio when the α-receptors are put into an excited state by giving β-blocker inderal to the patient, and graph A2 showing the amplitude ratio when the β-receptors are put into an excited state by giving α-blocker to the patient.

Graphs B0, B1, and B2 in FIG. 2 show the phase of each harmonic pulse wave spectrum wherein the beginning of the pulse wave has a phase of zero. Specifically, graph B0 shows the normal phase, graph B1 shows the phase when the α-receptors are put into an excited state by giving β-blocker inderal to the patient, and graph B2 shows the amplitude ratio when the β-receptors are put into an excited state by giving a-blocker to the patient.

The apparatus pertaining to the present embodiment explained below uses the results of the above-recorded medication delivery experiment for medication delivery control. That is, the apparatus pertaining to the present embodiment detects the pulse waves of the patient at regular intervals and runs a frequency analysis on them. If the amplitude and phase of the spectra in the pulse waves are in a state as shown in graphs A1 and B1 then α-blocker is given to the patient in order to pacify the excited α-receptors, if the amplitude and phase of the spectra in the pulse waves are in a state as shown in graphs A2 and B2 then β-blocker is given to the patient in order to pacify the excited β-receptors; the patient's blood pressure is stabilized in this manner.

B. Composition of the Embodiments

Figure 3:
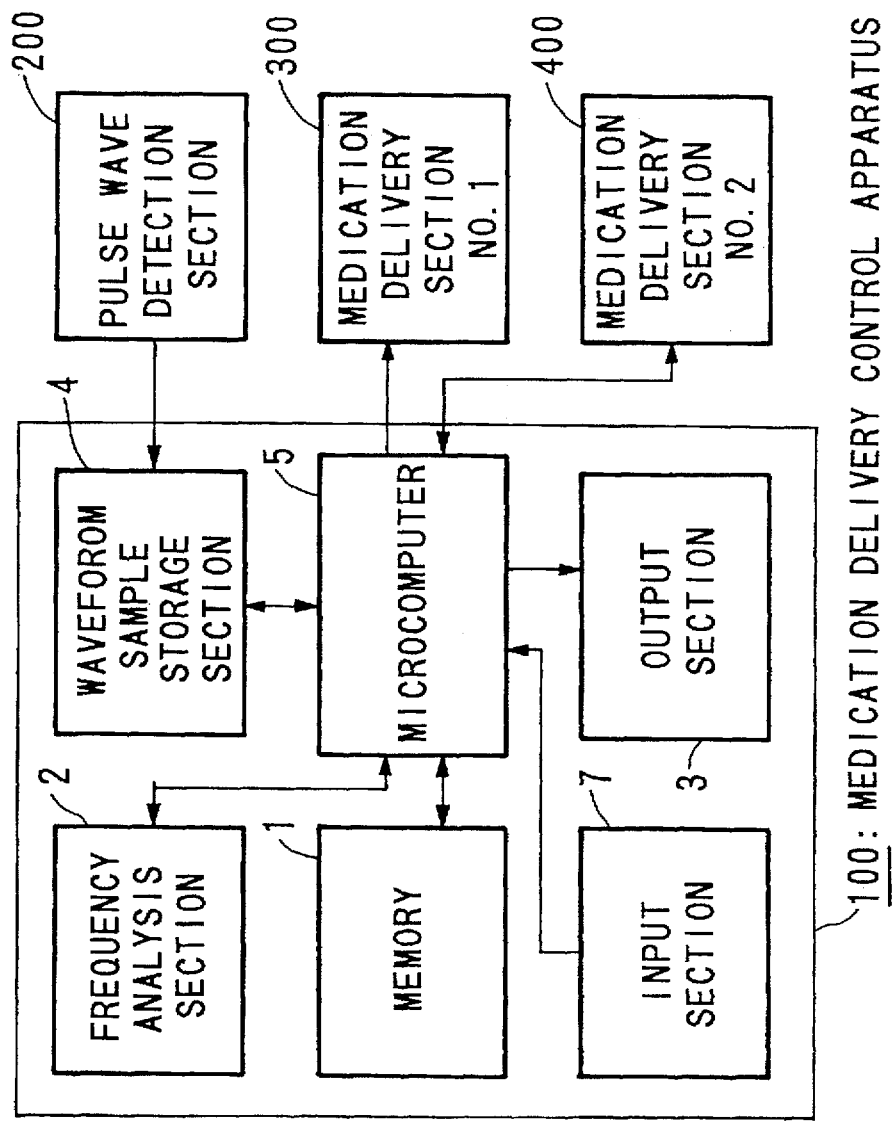
FIG. 3 is a block diagram showing the composition of the medication delivery control apparatus according to the first embodiment of the present invention.

FIG. 3 is a block diagram showing the composition of the medication delivery control apparatus (100) which pertains to the present embodiment. As seen in the diagram, pulse detector (200), medication delivery section no. 1 (300) and medication delivery section no. 2 (400) are attached to the medication delivery control apparatus (100). Pulse detector (200) employs a pressure detection part such as a skew gauge and a cuff to press the pressure detection part against the radial artery, measures the pressure on the pressure detector, and outputs a pulse wave signal (analog signal). Additionally, the pulse detector is used to measure the blood pressure, by measuring the blood pressure pulse wave from the skew gauge and outputting the result. Medication delivery sections no. 1 (300) and no. 2 (400) are composed of micropumps and their drive circuits, and depending on the control of medication delivery control apparatus (100), they dispense α-blocker and β-blocker to the respective patients.

Medication delivery control apparatus (100) is composed of memory (1), input section (7), output section (3), waveform sample storage section (4), frequency analysis section (2), and microcomputer (5). Memory (1) is a stable memory device composed of a RAM (random access memory) with a battery backup, and is used for the temporary storage of control data when the microcomputer (5) controls the parts of the medication delivery control apparatus (100). Furthermore, in a prescribed memory area of memory (1), the data represented by graphs A1 and B1 of the previously mentioned FIGS. 1 And 2 are stored as the α-dominant state defining data and the data represented by graphs A1 and B1 of FIGS. 1 and 2 are stored as the β-dominant state defining data. It is desirable to run the medication delivery experiment and frequency analysis of the pulse waves of as many patients as possible, and use the average of the data of graphs A1, B1, A2, and B2 received from each person as the dominant state defining data. Furthermore, the medication delivery control apparatus (100) pertaining to the present embodiment is composed such that, besides carrying out medication delivery control using fixed α-dominant state defining data and β-dominant state defining data, it can generate α-dominant state defining data and β-dominant state defining data based on the pulse wave spectrum of an individual patient, and carry out medication delivery control using α-dominant state defining data and β-dominant state defining data generated in this way. Thus in a special memory area in memory (1), α-dominant state defining data and β-dominant state defining data generated in this manner is stored.

Input section (7) is provided as a means for sending commands into microcomputer (5), and is composed of such items as a keyboard. Output section (3) is composed of such items as a printer and a display device, and according to the control of the microcomputer, the devices perform the recording of pulse spectra obtained from the patient, recording of the medication delivery, and the display of the pulse waves.

Figure 4:
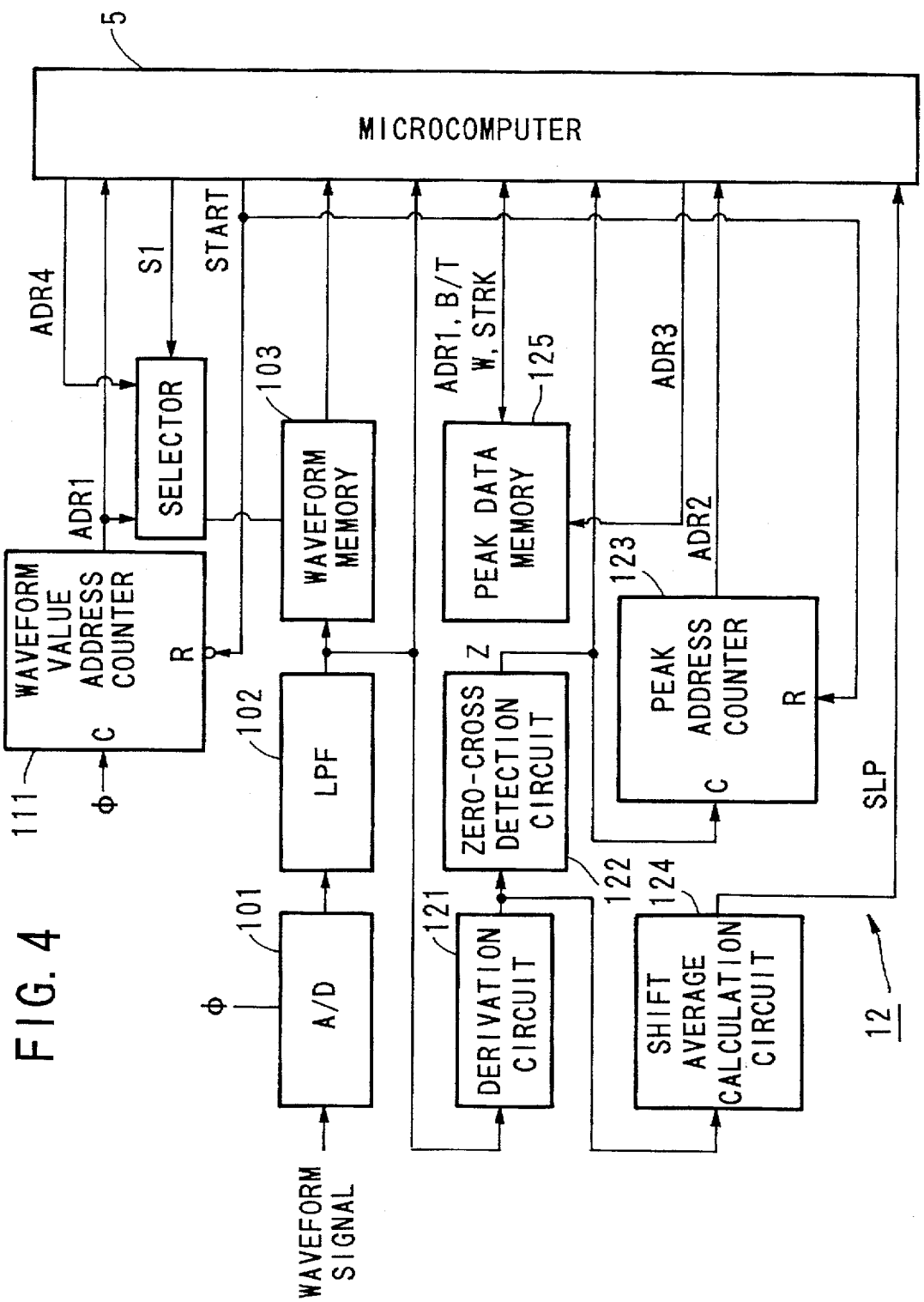
FIG. 4 is a block diagram showing the composition of the waveform sample storage section (4) of the same embodiment.

Waveform sample storage section (4), according to the control of the microcomputer (5), receives a waveform signal outputted by the pulse wave detector (200) and stores one wavelength (one cycle) of the received signal as a sample. Next, the composition of the waveform sample storage section (4) is explained with reference to FIG. 4. In FIG. 4, (101) is an A/D (analog to digital) converter, which converts the pulse wave signal output by pulse wave detector (200) into a digital signal according to a sampling clock φ with a fixed cycle. (102) is a low pass filter, which, for the digital signals sequentially output by the A/D converter (101), undergoes a procedure to remove the components above a fixed cutoff frequency, and outputs the results sequentially as the waveform value W. (103) is the waveform memory composed of RAM, and it sequentially stores the waveform value W received through the low pass filter (102). (111) is the waveform value address counter, and when the waveform gathering command START is output from the microcomputer (5), it counts the sampling clock φ and sends the results of the count to the address input end of waveform memory (103) as the waveform address ADR1 for writing in the waveform value W. This waveform address ADR1 is monitored by the microcomputer (5).

(121) is the derivation circuit, and it calculates the time derivatives of the waveform values sequentially output from the low pass filter (102). (122) is the zero-cross detection circuit, which outputs the zero-cross detection pulse Z when the waveform value's time derivative becomes equal to zero. More specifically, zero-cross detection circuit (122) is provided in order to detect the peak points on the waveform of the pulse wave as given in FIG. 5 as an example, and when the waveform values W corresponding to these peak points are input then it outputs zero-cross detection pulse Z. (123) is a peak address counter, which, when the microcomputer outputs the waveform gathering command START, counts the zero-cross detection pulses Z, and outputs the results of the count as the peak address ADR2. (124) is a movement average calculation circuit, which calculates the average value of the time derivatives of a pre-determined number of waveforms output from the derivation circuit (121) up until the appropriate time, and outputs the results as slope data SLP which represent the slopes of the waveform up until the appropriate time. (125) is a peak data storage memory provided in order to store the peak data discussed below.

Figure 7:
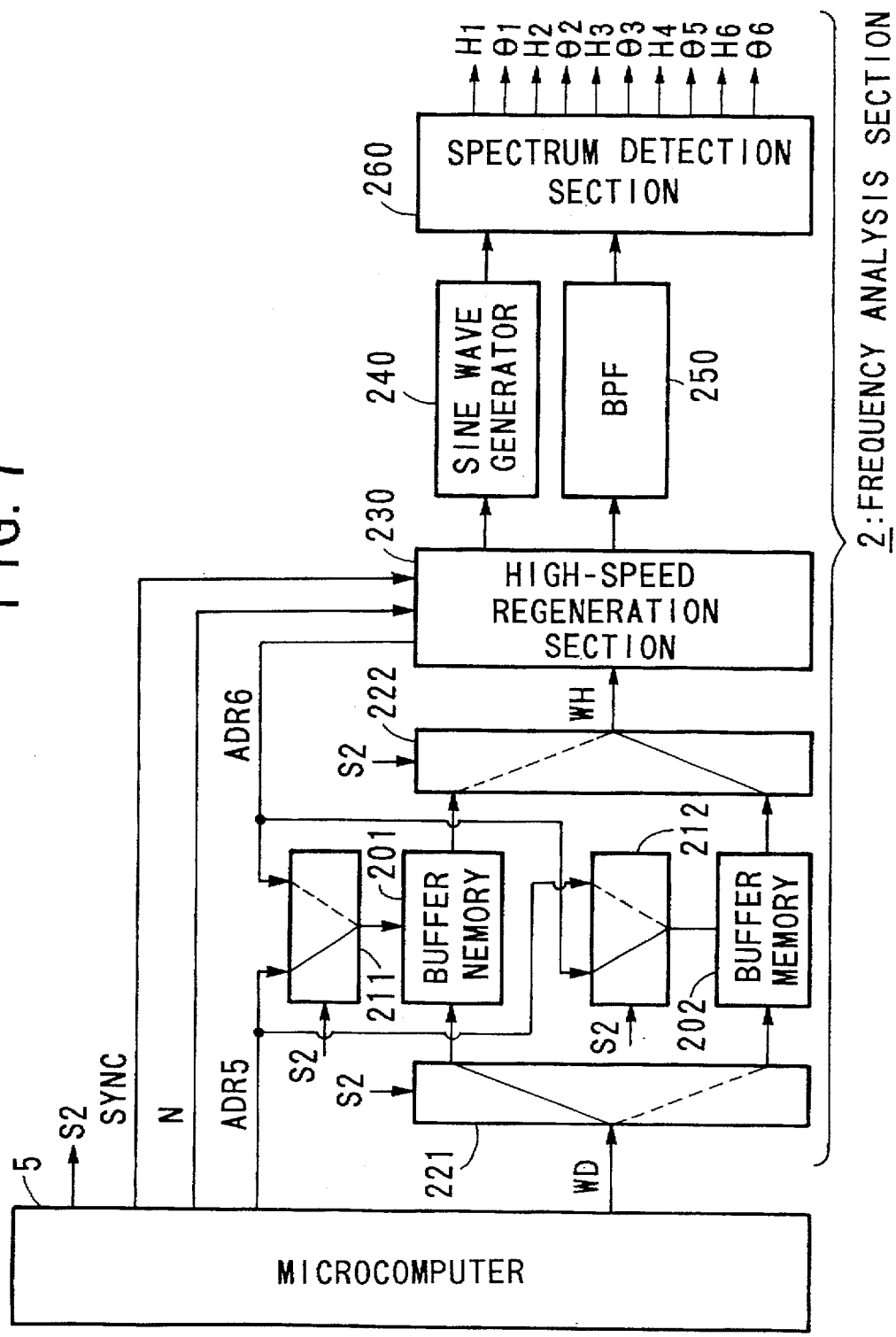
FIG. 7 is a block diagram showing the composition of the frequency analysis section (2) of the same embodiment.

Next the composition of the frequency analysis section (2) is explained in detail with reference to FIG. 7. This frequency analysis section (2) cyclically receives the waveform value WD through microcomputer (5) from the waveform memory (103) of the waveform sample storage section (4), regenerates the received waveform value WD at high speed, and calculates the spectrum composing the pulse wave by analyzing the frequency of each cycle. Additionally, this frequency analysis section (2) calculates first the fundamental spectrum, then the second harmonic spectrum, and so on, going through the respective spectra composing the pulse waves sequentially.

The microcomputer (5), when outputting the first waveform value WD of one cycle of a pulse wave to the frequency analysis section (2), in addition to outputting the synchronous signal SYNC and the number N of waveform values WD included in the cycle, switches the select signal S2. Additionally, microcomputer (5), while outputting one cycle of the waveform values WD, sequentially outputs the write-in address ADR5 which changes from 0 to N−1 in synchronization with the delivery of each waveform value WD.

The buffer memories (201) and (202) are provided for the collection of the waveform values WD output from the microcomputer (5). The distributor (221) outputs the waveform values WD of the pulse waves received through the microcomputer from the waveform sample storage section (4) to either buffer memory (201) or buffer memory (202) depending on the direction indicated by the select signal S2. Selector (222) selects the buffer memory indicated by the select signal S2 out of buffer memory (201) or buffer memory (202), and outputs the waveform value WH read from the buffer memory to the high-speed regeneration section (230) discussed below. Selectors (211) and (212) select either the write-in address ADR5 or the read-out address ADR6 (discussed below) generated by the high-speed regeneration section (230) according to the select signal S2, and delivers them to buffer memories (201) and (202).

Because there is switching control of the distributor (221), selector (22), and buffer memories (201) and (202) based on the select signal S2, while data is being written into buffer memory (201), data is being read out from buffer memory (202), and delivered to the high-speed regeneration section (230), and while data is being written into buffer memory (202) data is being read out from buffer memory (201) and delivered to the high-speed regeneration section (230).

High-speed regeneration section (230) is a means for reading out the waveform values corresponding to each cycle from buffer memories (201) and (202), and outputs the read-out address ADR6 by varying it over an interval of 0 to N−1 (wherein N is the number of waveform values to be read out). More specifically, this high-speed regeneration section (230), while the respective waveform values WD corresponding to a certain cycle are being written into one of the buffer memories, generates the above-mentioned read-out address ADR6, and repeatedly reads out all of the waveform values WD corresponding to the previous cycle from the other buffer memory. At this time, the generation of read-out address ADR6 is controlled so that all of the waveform values WD corresponding to a single cycle can always be entirely read out in a fixed period of time. The time interval for reading out all of the waveform values for a complete cycle corresponds to the degree of the spectrum being detected; that is, T for detecting the fundamental spectrum, 2T for the second spectrum, 3T for the third degree spectrum, and so on. Furthermore, the high-speed regeneration section (230) contains an interpolation mechanism which interpolates the waveform values WH read out from the buffer memories (201) and (202), and outputs them as the waveform values of a fixed sampling frequency m/T (m is a fixed integer).

Bandpass filter (250) has the fixed value 1/T as the central frequency of its pass band. Sine wave generator (240) is a variable frequency waveform generator, and, according to the control of microcomputer (5), it sequentially generates sine waves of period T, 2T, 3T, 4T, 5T, and 6T corresponding to the degree of the spectrum to be detected. Spectrum measurement section (260) measures the amplitudes $H_1$ to $H_6$ of each of the spectra of the pulse waves based on the output signal level of the bandpass filter (250) and also measures the phase ($\theta_1$ to $\theta_6$ of each of the spectra based on the difference between the phase of the output signal of the bandpass filter (250) and the phase of the sine wave output by the sine wave generator (240).

Microcomputer (5) controls the various sections of the present apparatus (100) in accordance with commands input through the input section (7). Furthermore, microcomputer (5) contains a clock circuit, and in the active mode for carrying out the medication delivery control, performs the respective procedures given below upon the passing of a standard time interval.

I. Controlling the Procedure to Enter the Waveform Signals Into the Waveform Sample Storage Section (4) and the Procedure to Sample a Single Wavelength of the Pulse Wave Each time a peak point of a pulse wave is detected due to the derivation circuit (121) and zero-cross detection circuit (122) within the waveform sample storage section (4), the various data given in the below examples are determined, and they are written into the peak data memory (125) in accordance with the table format shown in FIG. 6.

The Meaning of the Peak Data:

Waveform Value Address ADR1:

the write-in address ADR1 output from the waveform address counter (111) when the waveform value W output from the low pass filter (102) is either minimized or maximized, that is, the write-in address in the waveform memory (103) of the waveform value W corresponding to a minimum or maximum;

Peak Type B/T:
data showing whether the waveform value W written at the waveform address ADR1 is a maximum (Top) or a minimum (Bottom);

Waveform Value W:
the waveform value corresponding to the above-mentioned maximum or minimum;

Stroke STRK:
the variance of the waveform value from the previous peak value to the present peak value; and Slope Data SLP:
the average value of the time derivatives of a predetermined number of waveform values prior to the present peak value.

II. The Frequency Analysis of the Pulse Wave and the Determination of the Condition of the Patient The waveforms are sequentially read out from the waveform memory (103) within the waveform sample storage section (4) and output to the frequency analysis section (5) as waveform data WD. Then, the waveform spectrum output by frequency analysis section (5) is compared with the $\alpha$-dominant state defining data and $\beta$-dominant state defining data, and it is determined whether or not the patient is in a state of excitation of the $\alpha$-receptors or $\beta$-receptors.

III. Medication Delivery Control

Based upon the above determination, if the patient's $\beta$-receptors are in an excited state and the patient's blood pressure is at a value requiring medication, then a drive command is delivered to medication delivery section no. 2 and $\beta$-blocker is given; and if the patient's $\alpha$-receptors are in an excited state and the patient's blood pressure is at a value requiring medication, then a drive command is delivered to medication delivery section no. 1 and $\alpha$-blocker is given.

Figure 8:
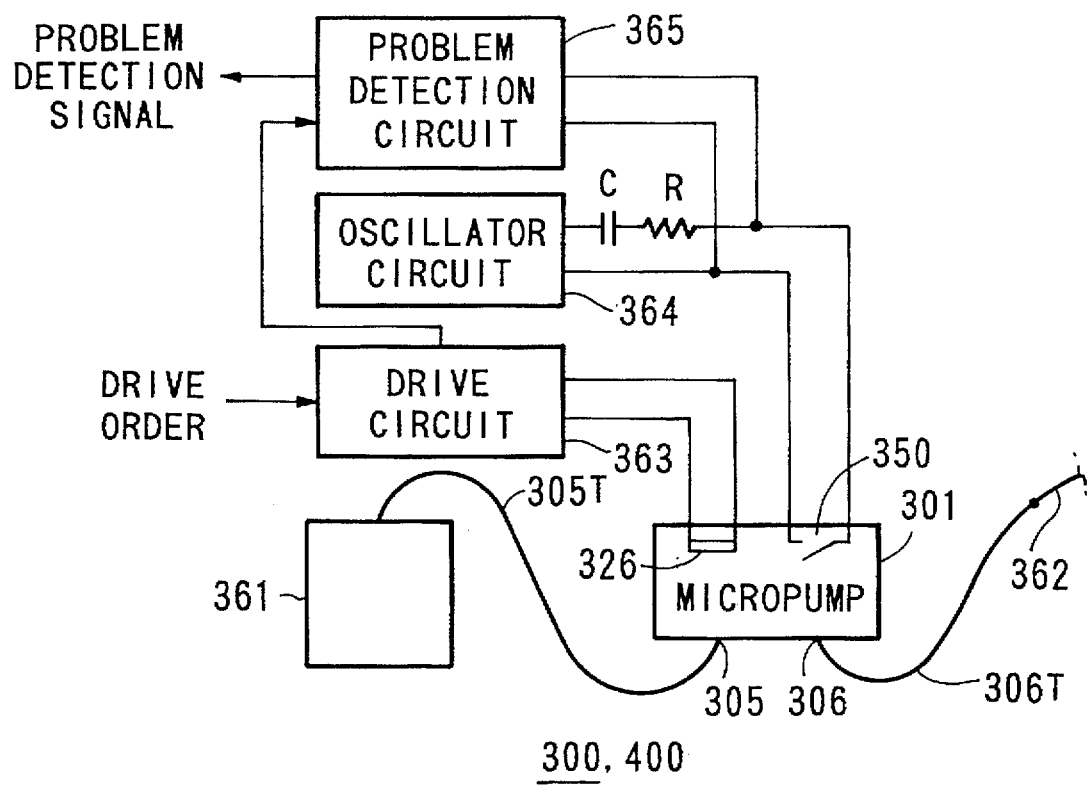
FIG. 8 is a diagram showing the composition of the medication delivery section (300) of the same embodiment.

FIG. 8 shows medication delivery section no. 1, or equivalently, medication delivery section no. 2 (400). In the diagram, (301) is a micropump, and its inlet port (305) is attached through the tube (305T) to the medication tank (361) which is filled with $\alpha$-blocker or $\beta$-blocker, and its outlet port (363) is attached through the tube (306T) to the syringe (362) for dispensing the medication. The drive circuit (363) generates a drive pulse of a standard level (approx. 100V) upon receiving a drive order from the microcomputer (5), and sends it to the piezoelectric element (326) which is the drive means for the micropump (301). Oscillator circuit (364) generates a number of pulses, the pulse widths of which are shorter than the pulse widths of the above-mentioned drive pulses, and sends them to the action detection switch (350) of micropump (301) through the capacitor (C) and the resistor (R). Here, the action detection switch (350) is constructed so that it is turned on only for a fixed period of time each time fluid is released from the outlet port (306) of micropump (301). Thus, when the micropump (301) is normally operating, a drive pulse is sent to the micropump (301) and each time the resulting release of fluid happens, the voltage at both ends of the action detection switch (350) is lowered. The problem detection circuit (365) commutes the voltage on both ends of the action detection switch (350), and sends out a problem detection signal if the voltage level taken from the commutation does not exhibit temporal changes corresponding to the drive pulses.

Figure 9:
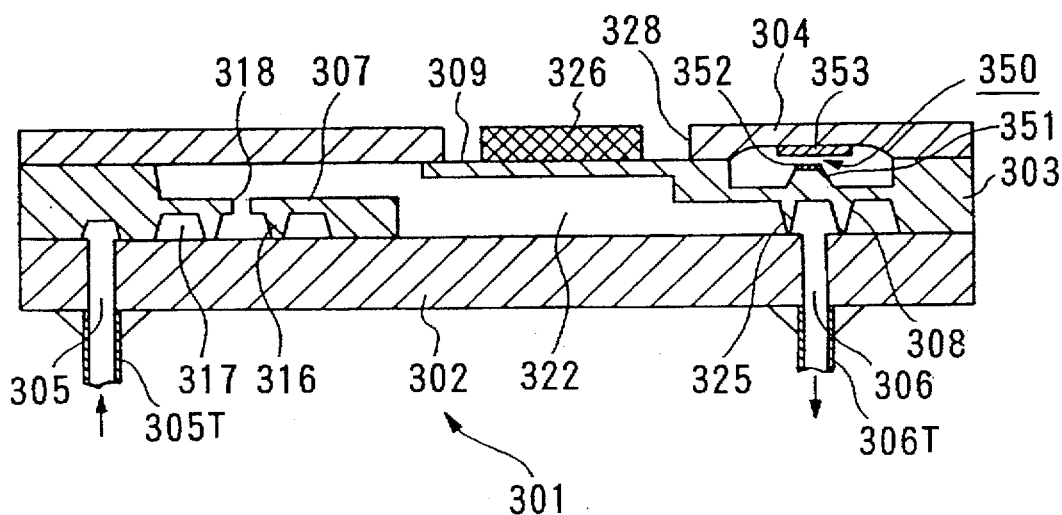
FIG. 9 shows a cross-sectional view of the composition of the micropump (301) of said medication delivery section.

FIG. 9 is a cross-sectional view of the micropump (301) comprising the medication delivery section. This micropump (301) is constructed by sandwiching the thin board (303) between the base board (302) and the surface board (304).

The base board (302) is composed of, for example, a glass board of thickness approximately 1 mm, and is provided with an inlet port (305) and an outlet port (306). To these ports, tubes (305T) and (306T) are attached with adhesive so as to prevent the occurrence of fluid leaks.

The thin board (303) is composed of, for example, a silicon board of thickness approximately 0.3 mm, and due to etching an inlet bulb (307) and an outlet bulb (308) are formed in addition to a diaphragm (309) between the bulbs. Furthermore, a pump chamber (322) beneath the diaphragm (309) and a pump flow system going through it are formed as well. Above the diaphragm (309), as a drive means, a piezodisc element (326) is attached.

Inlet bulb (307) is formed by covering over the base board (302), and at the approximate center of its top surface is formed a pass hole (318) as well as a valve (316) which protrudes down to surround the pass hole (318). The end section of this valve (316) impinges on the base board (302), and a chamber (317) is formed from the side of the inlet bulb (307) and the valve (316). This chamber (317) is attached to the inlet port (305) through a flow route not shown in the drawing. Outlet port (308) is comprised of a valve (325) which covers the opening of the outlet port (306) in a cap-like fashion.

Above the thin board (303) a surface board (304) composed of the same kind of glass board as the base board (302) is attached by an anode attachment method, and the top wall of a part of the flow route of the above-mentioned pump flow system is comprised of this surface board (304). On a part of this surface board (304) corresponding to the above-mentioned diaphragm (309) a window (328) is formed. The above-mentioned piezoelectric element (326) is attached through this window (328) on the surface of the exposed diaphragm (309) mentioned above. The thickness of the surface board is (304) is approximately 1 mm.

Next the action detection switch (350) is to be explained. This action detection switch (350) is provided in order to detect movements in a partition of the outlet bulb (308), and is comprised of a protuberance (351) which projects above said partition, an electrode (352) attached to the surface of this protuberance (351), and an opposite electrode (353) attached to the bottom of the surface board (304). Here, the output pulse of the oscillation route (364) is sent through the capacitor (C) and the resistor (R) to the electrodes (352) and (353). For the electrodes (352) and (353), such materials as Pt-Ir, W, Ta, Ni, Pt, Pd, Mo, Ti, polycrystalline Si, $WSi_2$, CP1, or CP2 may be used on the contacts.

C. Operation of the Embodiment

The operation of the present embodiment is explained below.

a. Medication Delivery Control Using Fixed $\alpha$-Dominant State Defining Data and $\beta$-Dominant State Defining Data When the mode is not especially set, the medication delivery control apparatus (100) pertaining to the present embodiment controls the delivery of medication to the patient based on $\alpha$-dominant state defining data and $\beta$-dominant state defining data which has been pre-stored in memory (1) as explained below. When delivering the medication, if medication tank (361) is traded with one filled with either $\alpha$-blocker or $\beta$-blocker, then the operator inputs the corresponding command from input section (7). Upon receiving this command the microcomputer (5) writes into the memory (1) the initial value of the remaining amount of $\alpha$-blocker and $\beta$-blocker (relative to the amount in one tankful).

As disclosed above, microcomputer (5) contains a clock circuit, and a timer interrupt signal is generated after the clock circuit measures out a fixed time interval. Then, upon generation of this timer interrupt signal the microcomputer (5) runs the timer interrupt routine shown in the flow chart of FIG. 10.

First, advancing to step S101, a procedure to gather waveforms and their peak data are run. Specifically regarding this procedure, first, the waveform gathering command START is output by microcomputer (5), and the waveform address counter (111) inside the waveform sample storage section (4) and the peak address counter (123) are reset. As a result, the count of the sampling clock φ is started by the waveform address counter (111), and that count value is delivered to the waveform memory (103) as the waveform address ADR1. Then, the radial artery waveforms detected by the pulse wave detector (200) are input into the A/D converter (101), sequentially converted into digital signals according to the sampling clock φ, and sequentially output through the low pass filter (102) as the waveform values W. In this way the output waveform values W are sequentially delivered to the waveform memory (103), and written into the appropriate memory area by the waveform address ADR1 depending on the time. Due to the above operation a series of waveform values W corresponding to the radial artery waveforms given as examples in FIG. 5 are collected in the waveform memory (103).

Additionally, in parallel with the above operation, the detection and writing into the peak data memory (125) of the peak data is performed as explained below. First, the time derivatives of the waveform values W output from the low pass filter (102) are calculated by the derivation circuit (121), and these time derivatives are entered into the zero cross detection circuit (122) and the movement average calculation circuit (124). The movement average calculation circuit in this way calculates the average values of a pre-set number of time derivatives (that is, movement average values) each time the time derivative values of the waveform values W are delivered. Here, if the waveform value is rising or at a maximum then the slope information is output as a positive value, and if the waveform value is lowering or at a minimum then the slope information is output as a negative value.

Figures 5, 6:
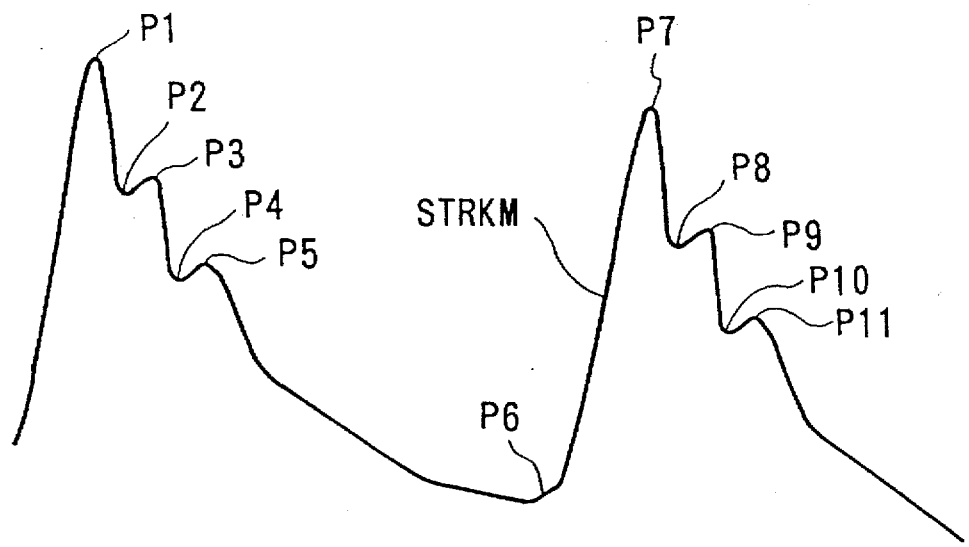
FIG. 5 shows a diagram demonstrating a pulse wave stored in waveform memory (103) of the same embodiment.
FIG. 6 shows a table showing the contents of the peak data memory (125) of the same embodiment.

Then, when a waveform value W corresponding to, for example, the maximum point P1 in FIG. 5, is output from the low pass filter (102), the time derivative "0" is output from the derivation circuit (121), and a zero-cross detection pulse Z is output from the zero-cross detection circuit.

As a result, due to the microcomputer (5), the relevant count value of the waveform value address counter (111) or waveform address ADR1, the waveform value W, the count value of the peak address counter or peak address ADR2 (in this case, ADR2=0), and the slope data SLP are entered. Also, because of the output of the zero-cross detection signal Z, the count value ADR2 of the peak address counter (123) becomes "1".

Then, microcomputer (5) generates the peak type B/T based on the sign of the slope data SLP. In the case of the output of a waveform value W of the maximum point P1 a positive value is output for the slope data, so the microcomputer (5) lets the peak data B/T correspond to a maximum value. Then, the microcomputer (1) sets the peak address ADR2 (in this case, ADR2=0) received from the peak address counter (123) as the write-in address ADR3, and writes in the waveform value W, the waveform address ADR1 corresponding to this waveform value W, the peak type B/T, and the slope data SLP into the peak data memory (125) as the first peak data. When writing in the first peak data, since there is no prior peak data, the generation and writing in of stroke data is not done.

Next, if a waveform value W corresponding to a minimum point P2 as shown in FIG. 5 is output from the low pass filter (102), a zero-cross detection pulse Z is output as above, and the write-in address ADR1, the waveform value W, the peak address ADR2 (=1), and the slope data SLP are all entered into the microcomputer (5). Then, due to the microcomputer, same as above, the peak type B/T (in this case, bottom B) is decided based on the slope data SLP. Additionally, the microcomputer delivers an address "1" smaller than the peak address ADR2 to the peak data memory (125) as the read-out memory ADR3, and the waveform value W first written in is read out. Then, due to the microcomputer (5), the difference between the waveform value W from the low pass filter (102) and the first waveform value W read out from the peak data memory (125) is calculated, and the stroke data STRK is determined. Then, the peak type B/T and the stroke data STRK determined in this way, in conjunction with the other data ADR1, W, and SLP are written into the peak data memory (125) as the second peak data in a memory area corresponding to the peak address ADR3="1". Subsequently, when the peak points P3, P4, etc. are detected the same procedure is carried out. Then, after the set time period has lapsed, the microcomputer (5) stops the waveform collection command START, and the collection of waveform values W and the peak data ends.

Similar to the above procedure, microcomputer (5) sequentially reads out the waveform values from the waveform memory (103) located in he waveform sample storage section (4), and sends them to the frequency analysis section (2) as the waveform data WD. Below, the procedure is explained with reference to FIGS. 11 and 12.

Figure 12:
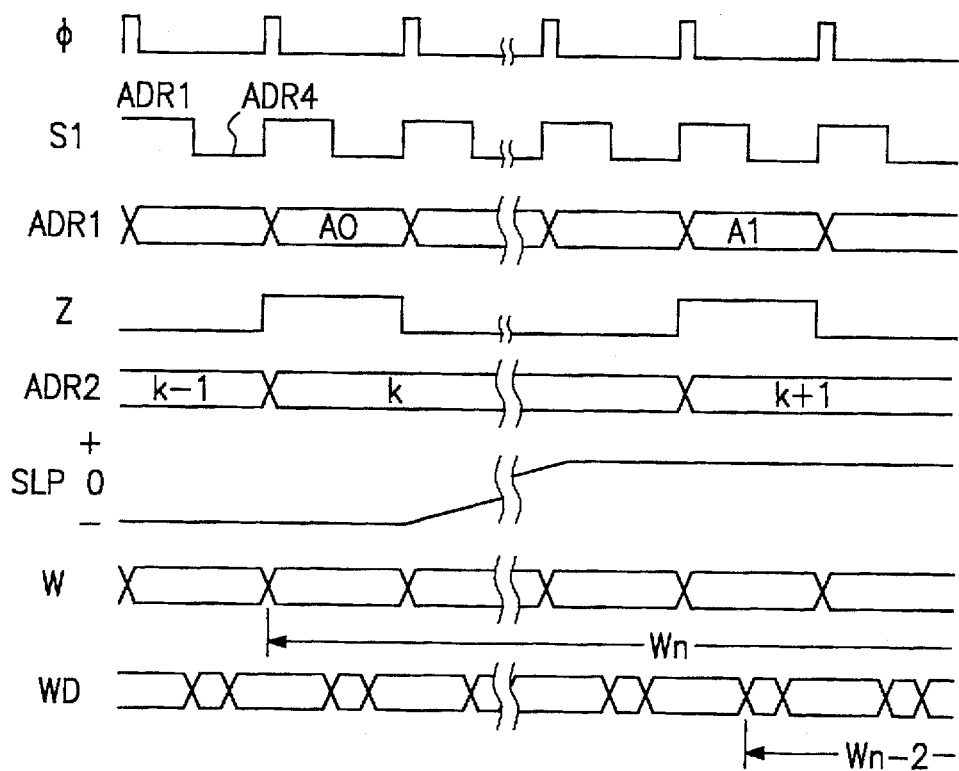
FIG. 12 shows a timing diagram for explaining the actions of the frequency analysis section (2) of the same embodiment.

As shown in FIG. 12, the select signal S1 is switched in time with the clock φ, and at the same time the write-in/read-out modes of the waveform memory (103) are switched.

Figure 11:
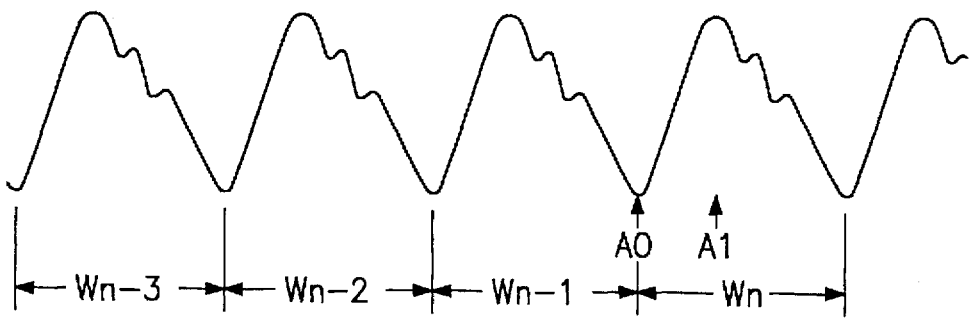
FIG. 11 is a diagram showing an example of the waveform of a pulse wave.

In FIG. 11, when the waveform value of a single wavelength of a pulse wave $W_n$ corresponding to a certain period is input into the waveform memory (103), first, a zero-cross detection signal Z is generated at the point at which the first minimum value corresponding to that period of the pulse wave is input, and the waveform address ADR1=$A_0$ is written into the peak data memory (125) (see FIG. 12). Subsequently, when the maximum value (address A1) is input into the waveform sample storage section (4), a zero-cross detection signal Z is again generated (see FIG. 12), and if the stroke between this maximum value and the minimum value (address $A_0$) directly before it is greater than a pre-determined value, then the address $A_0$ of the minimum value is written into the shift register within the microcomputer (5). The waveform address entered in this way is then output from the shift register two periods later, and is entered into the microcomputer (5) as the starting address of one period of the waveform value WD to be sent to the frequency analysis section (2). That is, in FIG. 11, when the address $W_n$ of a maximum value of a pulse wave $W_n$ corresponding to a certain period is written into the shift register, the starting address of the pulse wave $W_{n-2}$ of two periods ago (the address of the first minimum) already written into the same shift register is output from the shift register, and acknowledged by the microcomputer (5).

At this point the microcomputer (5) checks the contents of the above-mentioned shift register, determines the difference between the waveform address of the first minimum of pulse wave $W_{n-2}$ and the waveform address of the first minimum of the next pulse wave $W_{n-1}$, that is, the number N of waveform values contained in a single period of the pulse wave $W_{n-1}$, and outputs it to the frequency analysis section (2) with the synchronous signal SYNC. Also, the select signal S2 is switched synchronously with the synchronous signal SYNC, and the interior connection state of the distributor (221), the selectors (211) and (212), and the selector (222) go into the state shown by the full lines in FIG. 7.

Then, the microcomputer (5) sequentially increases the read-out address ADR4 from the waveform address of the first minimum value of the pulse wave $W_{n-2}$, and delivers them to the waveform memory (103) through the selector (112). Here, the read-out address ADR4 is changed at a faster rate (twice as fast, for example) than the write-in address. This is so that all of the waveform values corresponding to the pulse wave $W_{n-2}$ before pulse wave $W_{n-1}$ are read out before the maximum value of the pulse wave $W_{n+1}$ coming after pulse wave $W_n$ is entered into the waveform sample storage section (4). In this way, similar to the accumulation of wave pulses $W_n$ in the waveform memory (103), the microcomputer (5) reads out the waveform values WD of the pulse wave $W_{n-2}$ from two periods ago, sends them to the frequency analysis section (2), and sequentially delivers them through the distributor (221) to the buffer memory (201). While the waveform values WD are being sequentially delivered to the buffer memory (201) in this way, the write-in address ADR5 increases from 0 to N−1, and this write-in address ADR5 is delivered to the buffer memory (201) through the selector (211). As a result, at each memory area of each address 0 to N−1 in the buffer memory (201) each waveform value WD corresponding to the pulse wave $W_{n-2}$ is accumulated.

Similar to the above procedure, the read-out address ADR6 is output from the high-speed regeneration section (230), and delivered to the buffer memory (202) through the selector (212). As a result, each waveform value WD corresponding to the pulse wave $W_{n-3}$ a single period prior to pulse wave $W_{n-2}$ is read out, and entered into the high-speed regeneration section (230) through the selector (222).

Figure 13:
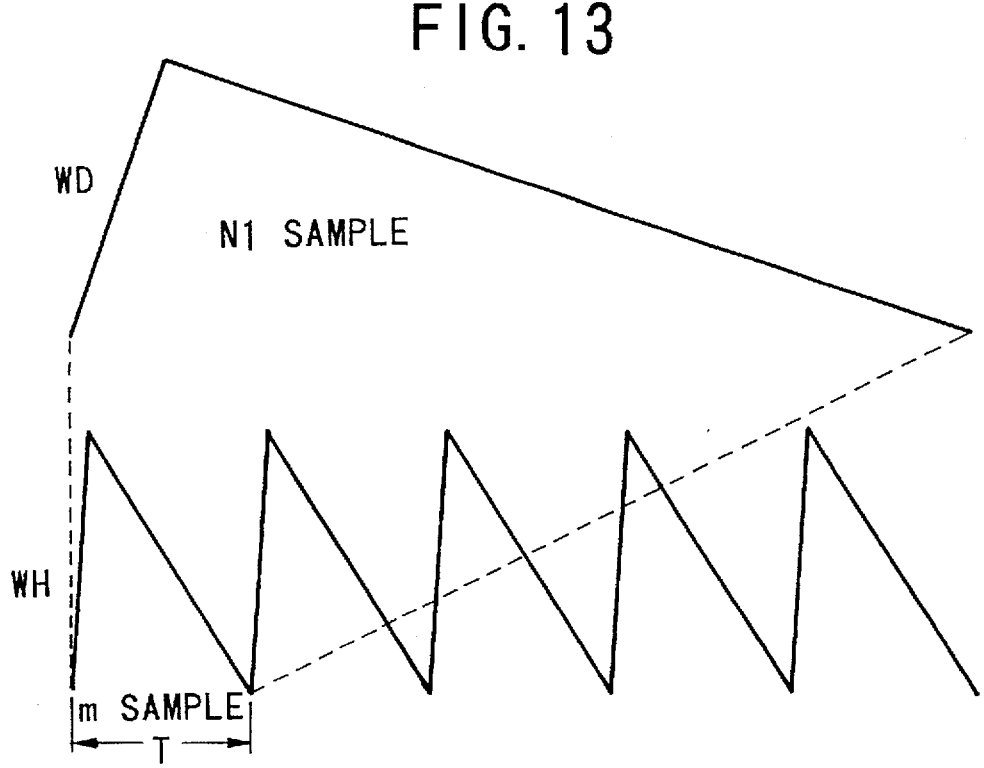
FIG. 13 is a waveform diagram for explaining the actions of the frequency analysis section (2) of the same embodiment.
Figure 14:
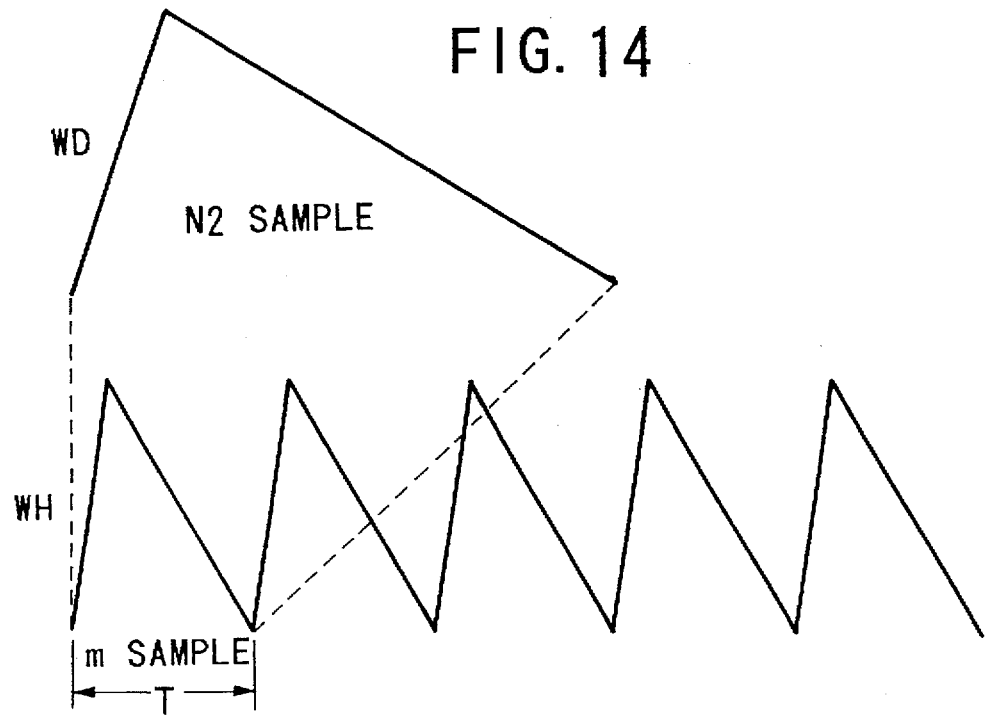
FIG. 14 shows a waveform diagram for explaining the actions of the frequency analysis section (2) of the same embodiment.

Here, the waveform values WD corresponding to the pulse wave $W_{n-3}$ contained in the buffer memory (202) are read out several times at a higher speed than the waveform values corresponding to the pulse wave $W_{n-2}$ contained in buffer memory (201) can be accumulated. On this occasion, so that the waveform values WD corresponding to the pulse wave $W_{n-3}$ may all be read out within the set time period, the speed increase of the read-out address ADR6 is controlled. That is, if the number of waveform values WD to be read out from the buffer memory (202) is greater than the value N1 as shown in FIG. 13, the high-speed regeneration section (230) increases the read-out address ADR6 at high speed, and if the number is a small value N2 as shown in FIG. 14, then it increases the read-out address at low speed, and it is made so that the read-out address ADR6 changes between 0 to N1−1 or 0 to N2−1 within the set time period T. Then, the waveform values WD read out in this way are given an interpolation calculation in the high-speed regeneration section (230), and are delivered to the bandpass filter (250) as the waveform values WH of a set sampling frequency m/T.

Figure 15:
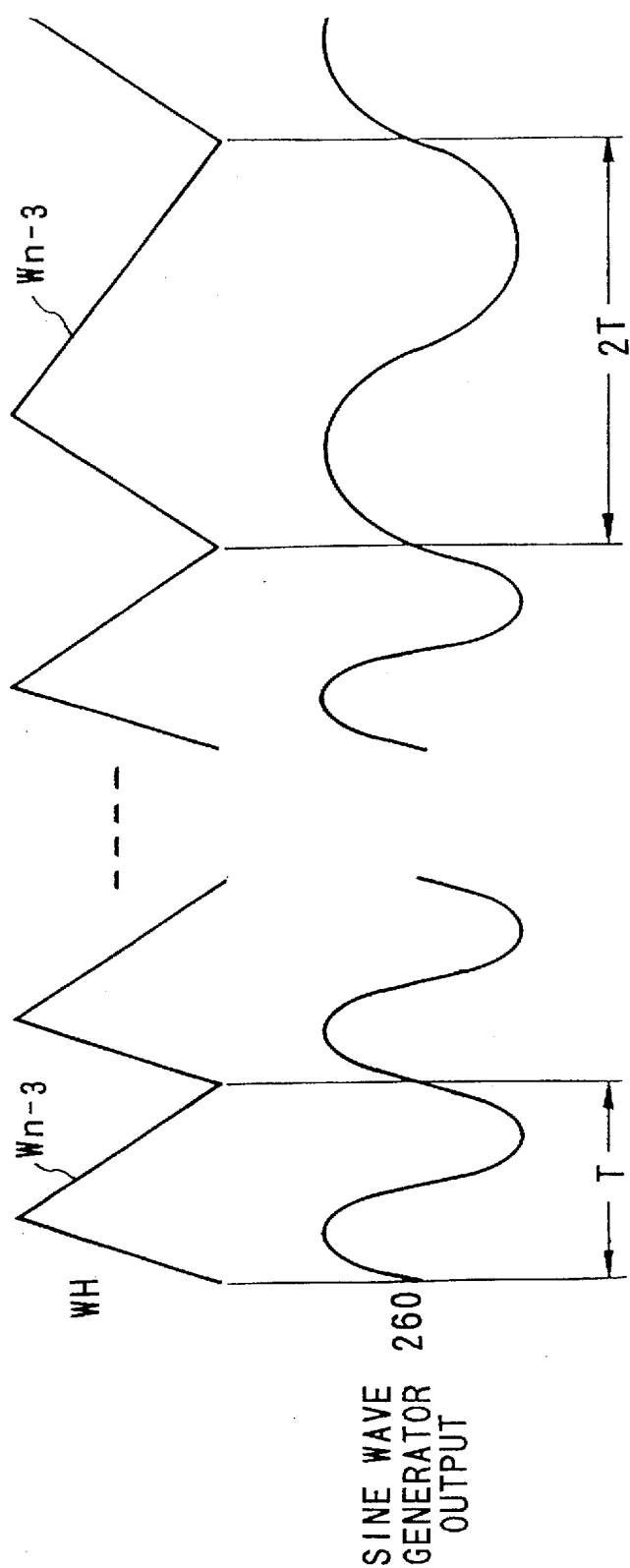
FIG. 15 shows a waveform diagram for explaining the actions of the frequency analysis section (2) of the same embodiment.

The bandpass filter (250) chooses and lets pass the signals with frequency 1/T out of the time series data of the waveform values WH, and delivers them to the spectrum measurement section (260). The sine wave generator (240) generates a sine wave of period T as shown in FIG. 15 and delivers it to the spectrum measurement section (260). The spectrum measurement section (260) measures the output signal level of the bandpass filter (250) depending on the frequency, outputs a representative value as the amplitude H1 of the fundamental wave spectrum of the pulse wave $W_{n-3}$, measures the phase difference between the output signal of the bandpass filter (250) and the sine wave generated by the sine wave generator (240), and outputs a representative value as the phase $\theta_1$ of the fundamental spectrum of the pulse wave $W_{n-3}$. For each representative value, the average shift value of the phase and the output signal levels corresponding to each wave, for example, fight before outputting the fundamental wave spectrum, are calculated.

Next the high-speed regeneration section (230) sets the speed increase of the read-out address ADR6 at one half that of the measurement of the above-mentioned fundamental wave spectrum so that all of the waveform values of the pulse wave $W_{n-3}$ can be read out within the set time period 2T, repeatedly reads out the waveform values WH corresponding to the pulse wave $W_{n-3}$, and delivers them to the bandpass filter (250) (see FIG. 15). Then, out of the time series data of the waveform values WH, the signals with a frequency 1/T, that is, the signals corresponding to the second harmonic waves of the pulse wave $W_{n-3}$ pass through the bandpass filter (250) and are delivered to the spectrum measurement section (260). As a result, the spectrum measurement section (260) measures and outputs the amplitude $H_2$ of the second harmonic spectrum of the pulse wave $W_{n-3}$. The sine wave generator (240) generates a sine wave with period 2T and delivers it to the spectrum measurement section (260) (see FIG. 15). As a result, the spectrum measurement section (260) outputs the phase $\theta_2$ of the fundamental spectrum of the pulse wave $W_{n-3}$.

Subsequently, the speed increase of the read-out address ADR6 is sequentially changed over to ⅓, ¼, ⅕, and ⅙ of the case for the fundamental wave spectrum while the periods of the sine waves generated by the sine wave generator (240) are changed to 3T, 4T, 5T, and 6T, the same procedure as above is repeated, and the amplitudes $H_3$ to $H_6$ and the phases $\theta_3$ to $\theta_6$ of the third degree to sixth degree harmonic spectra are output from the spectrum measurement section (260). The respective spectra of the pulse wave $W_{n-3}$ determined in this manner are entered into the microcomputer (5). Then, the microcomputer (5) calculates the number N of the waveform values WD corresponding to the pulse wave $W_{n-3}$ and the frequency $f=1/(N\tau)$ of the fundamental spectrum using the period $\tau$ of the clock $\phi$, and outputs them from the output section (3) in conjunction with the above-mentioned spectrum.

Subsequently, the pulse wave $W_{n+1}$ coming one cycle after the pulse wave $W_n$ gets up, and after its first maximum value is input into the waveform sample storage section (4), the microcomputer (5) generates the synchronous signal SYNC and outputs the number N of waveform values WD contained in the pulse wave $W_{n-2}$. Additionally, the select signal S2 gets switched, and the connection state of the distributor (221), the selectors (211) and (212), and the selector (221) goes into the state shown by the dotted lines in FIG. 7. Then, similar to the accumulation of the pulse wave $W_{n+1}$ in waveform memory (103), the microcomputer (6) reads out from the waveform memory the waveform values WD of the pulse wave $W_{n-1}$ two cycles before it and sends them to the frequency analysis section (2), and sequentially delivers them through the distributor (221) to the buffer memory (202). Similar to this procedure, the waveform values WD corresponding to the pulse wave $W_{n-2}$ one cycle before pulse wave $W_{n-1}$ are read out from the buffer memory (201), and after they are interpolated by the high-speed regeneration section (230) they are output as the waveform values WH. Then, for the waveform values WH corresponding to the pulse wave $W_{n-2}$, the same procedure is taken as for the pulse wave $W_{n-3}$, and the spectrum is thus determined.

Subsequently, the same procedure as above is followed for each pulse wave sequentially arising, and the spectra of the respective pulse waves are determined one after the other.

Figure 10:
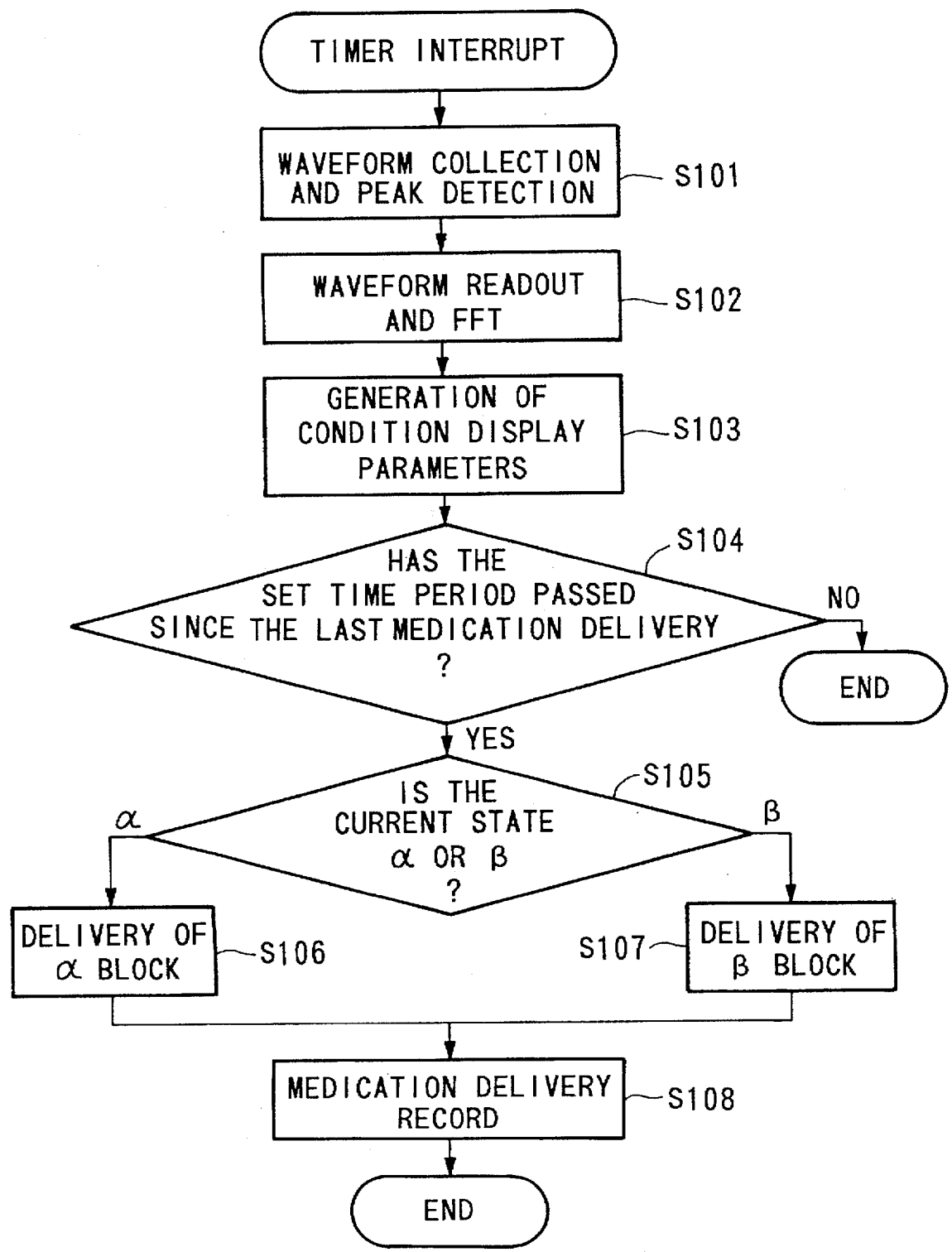
FIG. 10 is a flow chart showing the actions of the same embodiment.

Next, advancing to step S103 of FIG. 10, the microcomputer (5) collects the respective spectra of the pulse waves determined in S102 together with information on the present time and date into the memory (1), and writes the amplitude ratios between the respective harmonic spectra and the fundamental spectrum contained in the pulse waves, and the phases of the respective harmonic spectra into the memory (1) as the condition displaying parameters.

Next, advancing to step S104, referring to the time at which the last medication delivery was carried out recorded in the memory (1) and the output of the clock circuit, it is determined whether or not the required time interval has passed since the last delivery of medication. If the determination is "Yes" then the procedure advances to step S105, and if "No" then the timer interrupt routine is ended. The reason for including such a determination is to prevent the repeated delivery of the same type of blocker before the effects of the medication appear.

Next, advancing to step S105, the condition display parameters stored in the memory (1) are compared with the α-dominant state defining data and β-dominant state defining data. Here, if the condition display parameters agree with the α-dominant state defining data within some set error limits then the procedure advances to step S106. Then, the blood pressure value is determined by the pulse waves of the patient measured by the pulse wave detector (200), and if the value indicates the need for medication delivery then an activation order is sent to medication delivery section no. 1 (300) according to the set number of times for performing the delivery of α-blocker. If the condition display parameters agree with the β-dominant state defining data within some set error limits then the procedure advances to step S107, where, similar to step S106, if the blood pressure value of the patient indicates the need for medication delivery then an activation order is sent to medication delivery section no. 2 (400) according to the set number of times for performing the delivery of β-blocker. If the condition display parameters are different from either the α-dominant state defining data or the β-dominant state defining data then the timer interrupt routine is ended.

Figure 16:
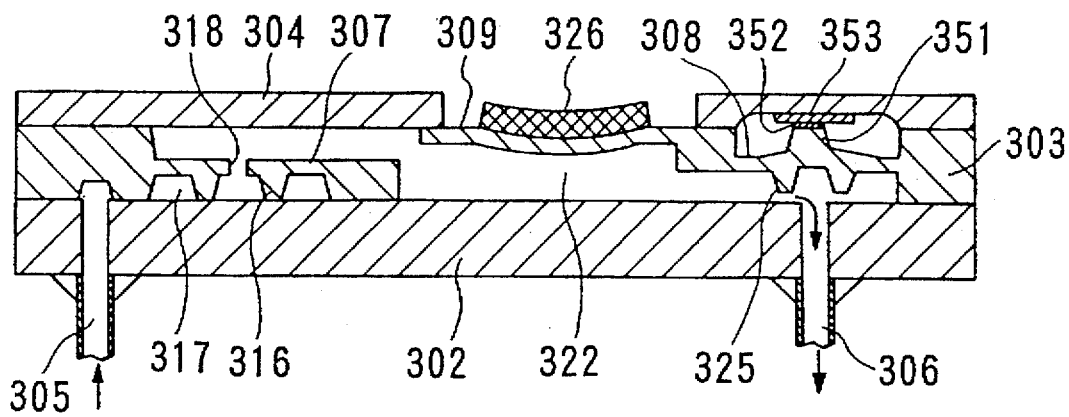
FIG. 16 is a diagram showing the actions of the micropump (301) of the same embodiment.
Figure 17:
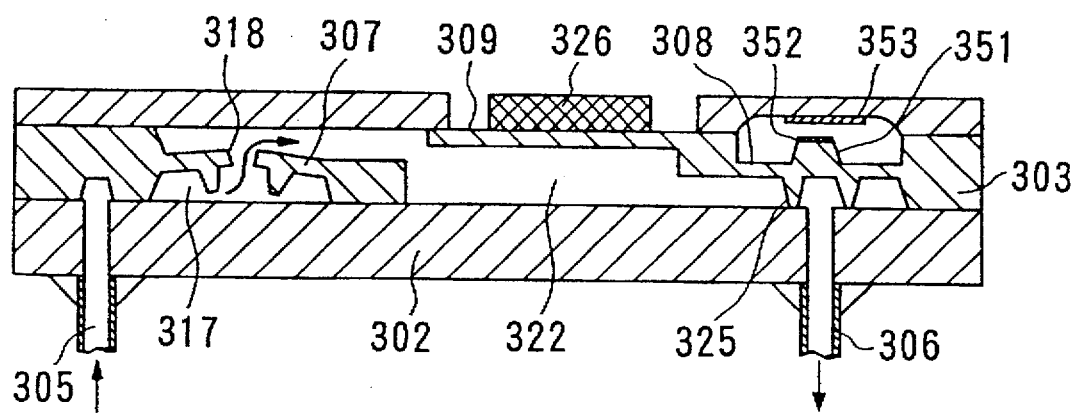
FIG. 17 is a diagram showing the actions of the micropump (301) of the same embodiment.

When the activation order is generated by the microcomputer (5), the following action is taken by the medication delivery section (300) or (400) which received it. First, the activation circuit (363) generates an activation pulse of a set level (approx. 100V) upon receiving an activation order from the microcomputer, and delivers it to the piezoelectric element (326) in the micropump (301). When this activation pulse is received, the piezoelectric element (326) changes shape as shown in FIG. 16, and the diaphragm (309) gets pushed down. As a result, the pressure inside the pump chamber (322) increases, the protuberance on the outlet bulb (309) gets pushed up, and the valve (325) comes away from the base board (302). Then, the blocker inside the pump chamber (322) flows through the seam between the valve (325) and the base board (302) and out of the outlet port (306), and is delivered to the patient through the tube (306T) and the syringe (362). Then, when the activation pulse goes down, as shown in FIG. 17, since the diaphragm (309) attempts to return to its original shape from the state in which it was bent inward, a reduction of pressure results in the pump chamber (322). Because of this, the outlet port (306) is closed off by the valve (325) of the outlet bulb (308) being pushed against the base board, and the protuberance on the inlet bulb (307) gets pushed upwards, and the valve (316) comes away from the base board (302). As a result, blocker flows in through the inlet bulb (305), and gets sucked into the pump chamber (322) through the seam between the valve (316) and the base board (302) and the pass hole (318). Subsequently, each time an activation pulse is received blocker is let out and sucked in as explained above.

While the micropump (301) is active, the voltage on both sides of its activation detection switch (350) is being monitored by the problem detection circuit (365). Because of such problems as jams in the needle, the block may not be released smoothly, and the relationship between the timing of the activation pulse and the timing of the "ON" state of the activation detection switch (350) may shift away from that of normal situations. The problem detection circuit (365) outputs a problem detection signal to the microcomputer (5) if it detects such a shift. The microcomputer (5), upon receiving the problem detection signal, displays an alarm through the output section (3) and prompts the user to change needles.

Upon the completion of step S106 or S107 the procedure advances to step S108, where according to the number of activation orders generated the dosage to be delivered is calculated, and this dosage, the type of block used (α-blocker/β-blocker), and the time of the medication delivery are written into the memory (1) as the medication delivery record data. In this way the medication delivery record data written into the memory (1) can be output through the output section (3) due to the input of a command through the input section (7). A doctor can use this medication delivery record data in order to diagnose any changes in the patient's condition. Furthermore, regarding step S108, the remaining amount of the blocker used in the current medication delivery is read out from the memory (1), the amount used in the medication delivery is subtracted from this amount and the result is written into the memory (1) as the new remaining amount. Here, if the remaining amount becomes lower than a set amount, then the microcomputer (5) sends a warning through the output section (3). The output section (3) prompts the user to change the medication tank through an alarm display such as a warning lamp. The warning may also be conveyed through the use of a sound. With the completion of the above step the timer interrupt routine is completed, and afterwards, after the passing of a set time interval, the timer interrupt routine is once again activated.

b. Pattern Memorization/Automatic Drive Mode

The user can set the pattern memorization/automatic drive mode as the activation mode by inputting a command through the input section (7). In this activation mode, the α-dominant state defining data and β-dominant state defining data are based on spectra of pulse waves taken from the patient, and afterwards, the α-dominant state defining data and β-dominant state defining data generated in such a manner are used in order to control the medication delivery. Below, the actions involved in this activation mode are explained.

Figure 18:
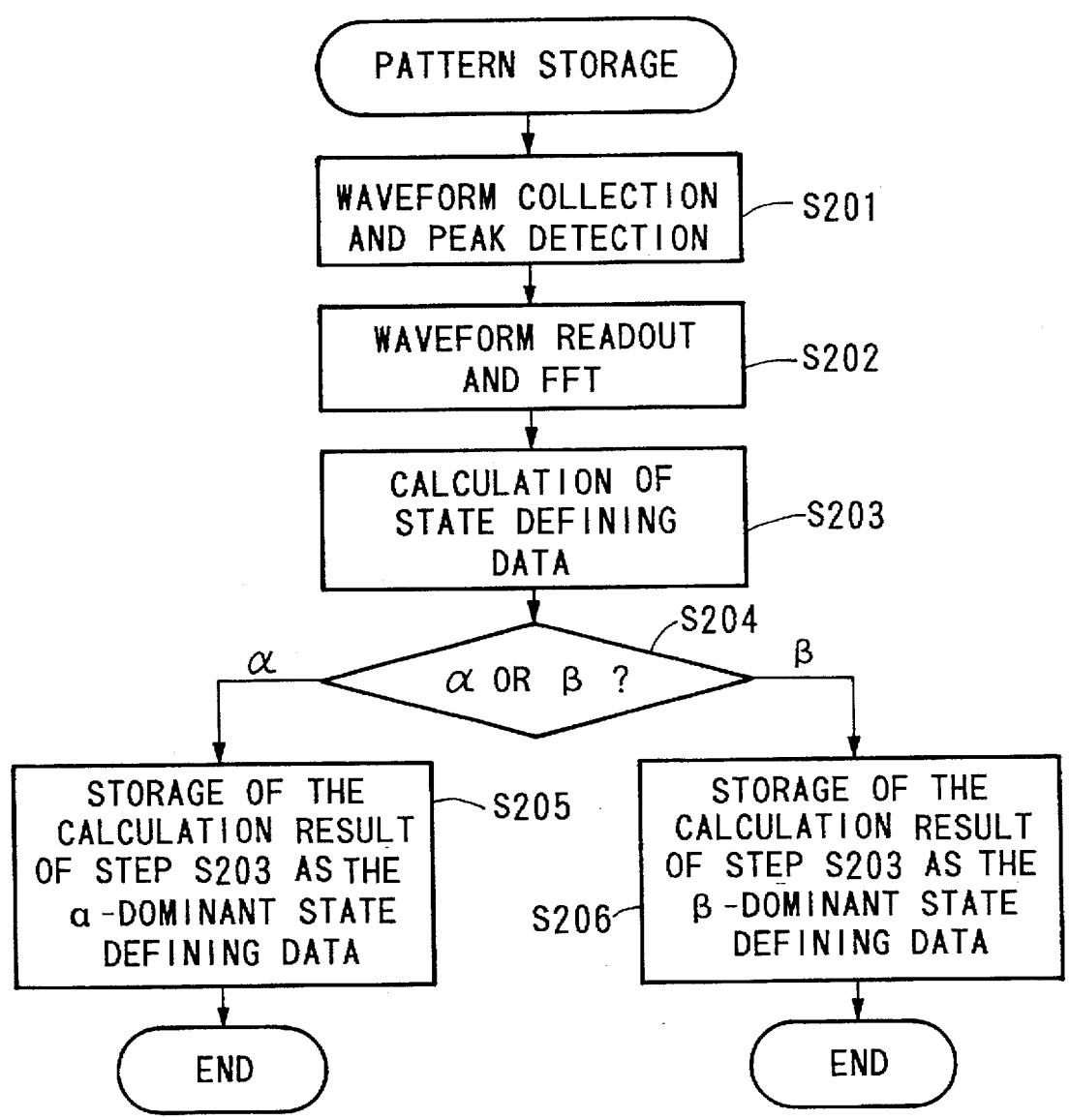
FIG. 18 is a time chart showing the actions of the same embodiment.

First, upon the starting medication delivery control using this activation mode, it is necessary to obtain the α-dominant state defining data and β-dominant state defining data. When the patient is in a state requiring α-blocker or β-blocker, the doctor enters commands to generate α-dominant state defining data and β-dominant state defining data into the input section (2). As a result, the pattern memorization routine shown in the flow chart in FIG. 18 is run by the microcomputer (5). First, advancing to step S201, the respective procedures for waveform collecting and peak detecting are run, then in step S202, the sampling procedure and FFT of a single wavelength of the pulse wave are run. The procedures in each of the steps are identical to those of steps S101 and S102 given in the above timer interrupt routine (see FIG. 10) and so the detailed explanation is skipped. Next the procedure advances to step S203, where the state defining data (the α-dominant state defining data and β-dominant state defining data) are calculated based on the spectra of the pulse wave obtained in step S202. Then, advancing to step S204, it is determined whether the generated state defining data are α or β, and according to this determination, the calculation result in step S203 is written into the memory (1) as either α-dominant state defining data (step S205) or β-dominant state defining data (step S206). After the α-dominant state defining data and β-dominant state defining data are entered into the memory (1) in this way, the start commands for medication delivery control based on the relevant state defining data are entered into the input section (2). According to this, as explained above, the timer interrupt routine is run at fixed time intervals. However, in this case, the α-dominant state defining data and β-dominant state defining data taken from the patient in the above manner, not standard state defining data which has been pre-entered into the memory (1), are the basis for medication delivery control.

The Second Embodiment

The composition of the second embodiment of the present invention is shown in FIG. 19. In the figure, (700) is a stationary medication delivery control apparatus to be fixed to the side of a hospital bed, (800) is a portable medication delivery control apparatus to be attached to the patient, and these apparatuses have a composition similar to the medication delivery control apparatus (100) of the first embodiment. Accordingly, regarding these apparatuses (700) and (800), the parts corresponding to the respective parts in the above-mentioned medication delivery control apparatus (100) are given the same reference symbols and their explanation is omitted, while below, only the parts differing from the apparatus (100) are explained.

Both medication delivery control devices (700) and (800) are provided with microcomputers (5) with I/O interfaces (6) in order to carry out mutual communication. Exterior devices such as the pulse wave detection section (200), medication delivery section no. 1 (300), and medication delivery section no. 2 (400) are connected to the stationary medication delivery control apparatus (700) or the portable medication delivery control apparatus (800) by means of their respective cables (200C), (300C), and (400C). Inside each cable (200C), (300C), and (400C) is a signal line and a power line; the transfer of signals between the medication delivery control apparatus and each exterior device is performed through the signal lines, while the delivery of electricity is performed through the power lines.

The portable medication delivery control apparatus (800) has a power control section (8b) for delivering power from a battery which is charged through charging electrodes (8d) to the interior sections of the apparatus and to the exterior devices through the above-mentioned power lines. Because the portable medication delivery control apparatus (800) uses a battery as its power source, in order to save energy, the delivery of power is controlled by the power control section (8b) through the microcomputer (5). That is, under the control of the microcomputer (5), when the timer interrupt routine is activated, power is delivered from the power control section (8b) to the interior sections of the apparatus only while it is necessary, and otherwise, power is only delivered to the microcomputer (5). Furthermore, power is delivered to the pulse wave detection section (200) only when the A/D converter inside the waveform sample storage section (4) is sampling the waveform values, and power is delivered to the medication delivery sections (300) and (400) only when medication delivery is being carried out as per steps S106 and S107 in the timer interrupt routine. Additionally, the power control section (8b) employs a voltage monitoring circuit which outputs an alarm signal when the output voltage of the battery becomes lower than a set value. This alarm signal is sent to the microcomputer (5), and upon receiving such an alarm signal the microcomputer (5) generates a warning by activating a warning means such as an LED or a warning sound generator.

The stationary medication delivery control apparatus (700) has a power source (8a), and this power source (8a) relies on a commercial power source in order to deliver power to the interior of the apparatus as well as such exterior devices as the pulse wave detection section. Furthermore the output voltage of the power source (8a) is designed to be output to the voltage output electrodes (8c), the battery in the portable medication delivery control apparatus (800) can be charged by connecting the charging electrodes (8d) to these electrodes (8c).

When each medication delivery control apparatus (700) and (800) is used individually, the actions are identical to those of the first embodiment given above so the explanation is omitted.

The medication delivery control apparatuses (700) and (800) of the present embodiment obtain their data through the I/O interfaces (6), and the following uses are possible.

1) The portable medication delivery control apparatus (800), the pulse wave detection section (200), medication delivery section (300), and medication delivery section (400) are connected to the stationary medication delivery control apparatus (800), and while charging the battery in the portable medication delivery control apparatus (800), the stationary medication delivery control apparatus (700) is used to obtain the α-dominant state defining data and β-dominant state defining data of the patient which are entered into memory (1).

2) The microcomputer (5) reads out the α-dominant state defining data and β-dominant state defining data stored in memory (1) in the stationary medication delivery control apparatus (700), and sends them to the portable medication delivery control apparatus (800) through the I/O interface (6). The data in the portable medication delivery control apparatus (800) go through the I/O interface and the microcomputer (5) and are written into memory (1).

3) The pulse wave detection section (200), medication delivery section no. 1 (300), and medication delivery section no. 2 (400) are connected to the portable medication delivery control apparatus (800), the commands for commencement of medication delivery control are entered, the timer interrupt routine explained in the first embodiment given above is run at regular time intervals, and medication delivery is performed based on the α-dominant state defining data and β-dominant state defining data received from the stationary medication delivery control apparatus (700). At this time, the patient is free to move from his hospital bed. Additionally, at this time, if the output voltage of the battery within the portable medication delivery control apparatus (800) becomes less than a set value, then an alarm signal is generated, and a warning is issued by the microcomputer (5) upon receiving the alarm signal.

4) After a set period of time, or the display of an alarm for replacing the medication tank, the patient returns to the hospital bed. Then, the portable medication delivery control apparatus (800) is connected to the stationary medication delivery control apparatus (700), and while the battery in the portable medication delivery control apparatus (800) is being charged, the medication delivery record (the times at which the medication was delivered, the type of blocker given) stored in memory (1) in the portable medication delivery control apparatus (800) is sent to the stationary medication delivery control apparatus (700). This medication delivery record is added to the medication delivery record stored in memory (1) up until that point in the stationary medication delivery control apparatus (700). In this way a record of the medication delivery data remains in memory (1) in the stationary medication delivery control apparatus (700), and a doctor can use the medication delivery data output from the output section (3) in order to make a diagnosis of any changes in the patient's condition. Furthermore, at this time, the doctor can, if necessary, re-create the α-dominant state defining data and β-dominant state defining data by using the stationary medication delivery control apparatus, and send them to the portable medication delivery control apparatus (800). Subsequently, if the patient wishes, the control of the delivery of medication may be performed by the portable medication delivery control apparatus (800) by using the same procedure as given in steps 2 and 3 given above.

The Third Embodiment

In the first and second embodiments given above, the data taken from the waveform spectra were used in the form of condition display parameters (waveform parameters, as in steps S102 and S103 of FIG. 10), and it was determined whether or not to deliver medication based on these condition display parameters (step S105). On the other hand, the present embodiment uses the method given in Japanese Patent Application No. Hei 5-1431, the disclosure of which is hereby incorporated by reference. According to this method, the value of each element in the Four Element Concentration Constant Model, which models the patient's circulatory movement based on the pulse waves taken from the patient, is determined and the results are used as the condition display parameters.

Here, the Four Element Concentration Constant Model observes the four parameters which govern the action of the human circulatory system, that is, the inertia of the blood in the central arteries, the blood vessel resistance in the central arteries due to blood viscosity (viscous resistance), the compliance of the blood vessels in the central arteries (viscoelasticity), and the blood vessel resistance in the capillaries (viscous resistance), and models them on an electric circuit.

Figure 20:
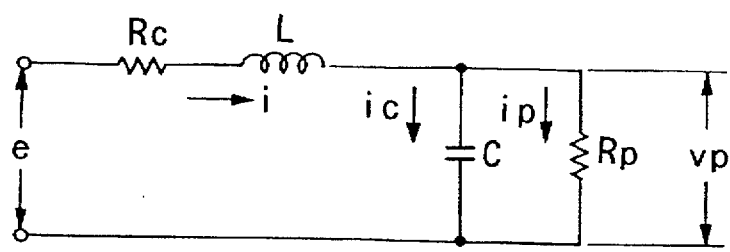
FIG. 20 is a circuit diagram showing the four element concentration constant model used in the third embodiment of the present invention.

FIG. 20 shows the circuit diagram for the Four Element Concentration Constant Model. Below, the relationships between the respective elements which make up the Four Element Concentration Constant Model and the above-mentioned parameters are shown.

Inductance L:
the inertia of the blood of the central arteries

[dyn·s²/cm⁵]

Capacitance C:
the compliance of the blood vessels of the central arteries

[cm⁵/dyn]

The compliance is a measure of the softness of the blood vessels, and it refers to the viscoelasticity.

Electrical Resistance $R_c$:
the blood vessel resistance due to the blood viscosity in the central arteries

[dyn·s/cm⁵]

Electrical Resistance $R_p$:
the blood vessel resistance due to the blood viscosity in the capillaries

[dyn·s/cm⁵]

Additionally, the electrical currents i, $i_p$, and $i_c$ flowing in the electrical circuit correspond to the blood flow [cm³/s] flowing in the respective sections. Furthermore, the input voltage e applied to this circuit corresponds to the pressure [dyn/cm²] at the origin of the aorta. Also, the voltage $v_p$ across the capacitance C corresponds to the pressure [dyn/cm²] at the radial artery.

Regarding the present embodiment, after the microcomputer (5) has read out a single cycle of the pulse wave from the waveform memory (103) as per step S102, a simulation is run on the above-mentioned Four Element Concentration Constant Model in which an electronic signal is given which corresponds to a pressure wave in the aortic origin. Then, the values of the respective elements in the Four Element Concentration Constant Model for the pulse wave read out from the waveform memory (103) are calculated, and the results of the calculation are used as the condition display parameters. A detailed description of the method of determining the four Element Concentration Constant Model is given in the above-mentioned Japanese Patent Application No. Hei 5-1431 and therefore such an explanation is omitted. Then, regarding step S105, the values of the respective elements of the Four Element Concentration Constant Model for the α-dominant state defining data and β-dominant state defining data, which were prepared as pre-determined conditional parameters, are compared with the above-mentioned condition display parameters, and the condition of the patient is determined.

The Fourth Embodiment

In this fourth embodiment, the distortion d of the pulse wave is calculated from the frequency spectrum of the pulse wave, and the medication delivery control is carried out based on the distortion.

That is, the microcomputer (5) determines the distortion d from the frequency spectrum of the pulse wave obtained from the frequency analysis section (2) with the use of the following equation.

$$d = \sqrt{(A2^2 + A3^2 + \ldots + An^2)}/A1$$

wherein A1 is the amplitude of the fundamental waves of the pulse wave

A2, A3, ..., An are the amplitudes of the second through n-th degree harmonic waves A table giving the relationship between the patient's condition and the distortion d is pre-stored in the memory (1). Then, after determining the distortion by the above equation, the microcomputer (5) measures the patient's condition using the table stored in memory (1), and controls the medication delivery sections no. 1 (300) and no. 2 (400) according to the results.

It is also possible to calculate the distortion d by the following equation.

$$d = (A2 + A3 + \ldots + An)/A1$$

Furthermore, the distortion d may be determined by sampling the low frequency and high frequency components of the pulse waves by inputting the pulse waves into low pass and high pass filters, then obtaining the direct current signals W1 and W2 by rectifying and smoothing these high frequency and low frequency components, and taking W2/W1.

Examples of Modification

1) In the first and second embodiments given above the pulse wave spectra were determined by FFT's, but it is also possible to use another frequency analysis method such as a MEM (maximum entropy method).

2) The delivery of α-blocker and β-blocker is carried out when the waveform parameters of the pulse waves fulfill some set conditions, but the medication delivery control may also be carried out by storing in memory the pulse wave itself in a state requiring the delivery of α-blocker and β-blocker and comparing the measured pulse wave to this stored pulse wave.

Figure 21:
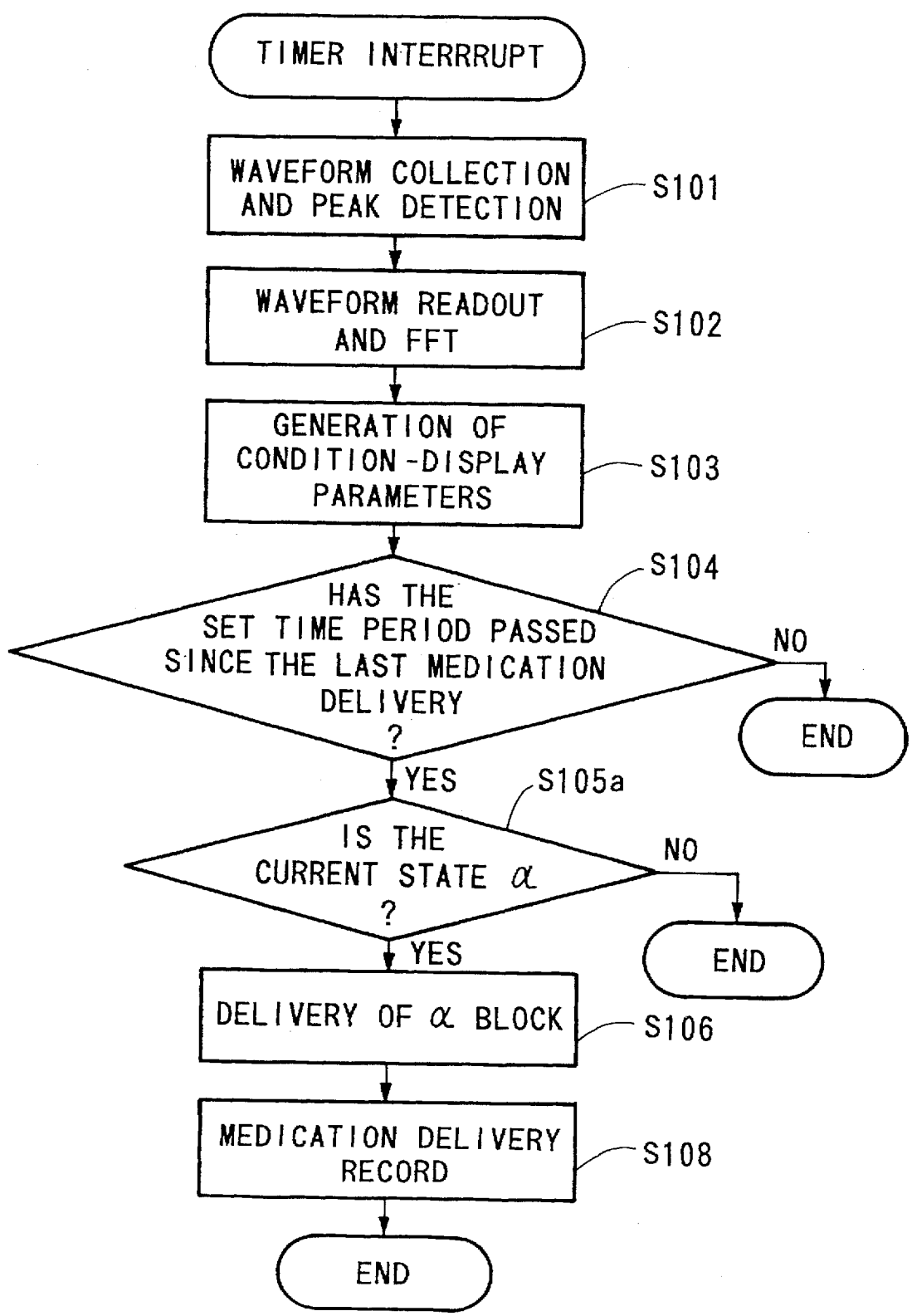
FIG. 21 is a flow chart showing the actions of a modified example of the above embodiments.

3) In the embodiments given above, examples are given in which two types of blocker are used, but it is possible to modify the above embodiments to use only one blocker, or to modify them to use three or more blockers. For example, if only the delivery of α-blocker is necessary, then medication delivery section no. 2 (400) may be erased from the composition shown in FIG. 3, and use only medication delivery section no. 1 (300). Also, everything after step S105 in the timer interrupt routine (FIG. 10) run at regular intervals by the microcomputer (5) may be changed to what is shown in FIG. 21. That is, if the result of step S104 is "Yes", then it is determined whether or not the present state of the patient is an α-dominant state, and if the result is again "Yes", then α-blocker is delivered (step S106) and the information is recorded (step S108), and if the result is "No", then the timer interrupt routine is ended without the delivery of medication.

4) In the above embodiments, a set amount of blocker medication was delivered all at once when the α-dominant state or β-dominant state was reached, but the manner of delivery of medication is not limited to this. For example, it is also possible to deliver nifedipine. Also in this case, it is possible to deliver the medication by setting the control method, that is, if an α-dominant state or β-dominant state is detected, delivering a set amount of medication at a certain time, then delivering another set amount of medication after the elapsation of a set time period, and so on, so that the medication is delivered several times according to a pre-set program.

5) In the above embodiments the delivery of medication was through a syringe, but the means for delivering medication are not limited to this. For example, such varying medication delivery methods as transdermal delivery, intravenous delivery, intraarterial delivery, abdominal delivery, oral delivery, and rectal delivery may also be used.

6) The present invention is not limited to the control of the delivery of circulatory activants, and it is possible to apply to other purposes. For example, such needs as the delivery control of prostaglandin (an arterial expansion agent) for the treatment of arteriosclerosis obliterans, the automatic control of intravenous drip, or the delivery control of heparin during dialysis can all be met by the apparatus pertaining to the present invention.

7) The medication delivery means is not limited to a micropump using silicon micromachining as given in the above embodiments, but it is also possible to utilize such fluid delivery pumps as syringe style, rotary style, or balloon style pumps in the medication delivery control apparatus of the present invention.

8) In the above embodiments the patient's condition was diagnosed based on the pulse wave at the radial artery, but it is also possible to base the medication delivery diagnosis on the analysis of the pulse waves elsewhere, such as the pulse waves of the blood vessels in the finger. Additionally, in the above embodiments, after deciding the necessity of medication delivery based on the waveform parameters, the final decision of whether or not to deliver medication was based on the determination of the blood pressure, but it is also possible to make the final decision by directly measuring the interior pressure of the blood vessels.

9) In the above embodiments, the detection of an α-dominant state or β-dominant state in the patient was based on the spectral patterns of the pulse waves, but it is also possible to base the detection on specific changes in the spectrum.

Figure 22:
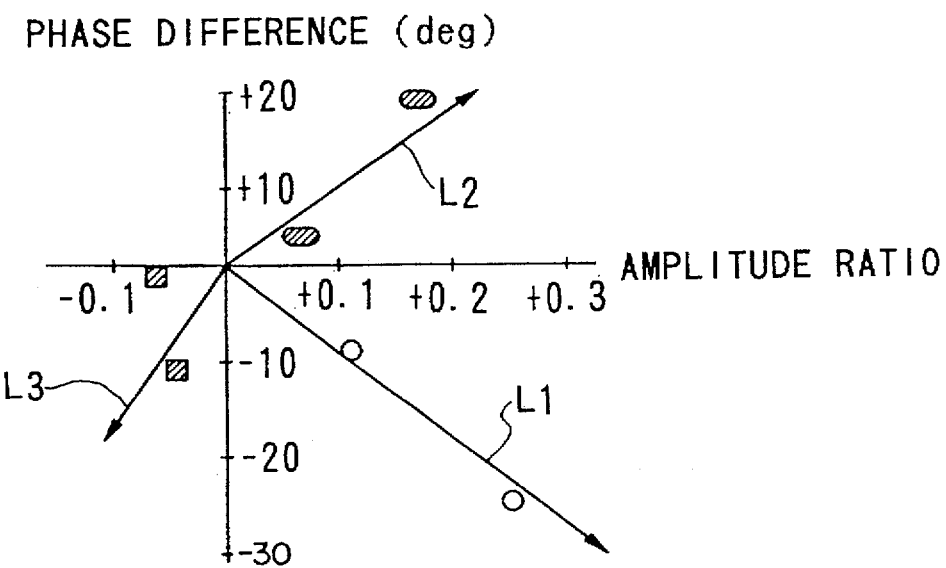
FIG. 22 is a diagram showing the change in the amplitude and phase of the second degree harmonic wave of a pulse wave due to medication delivery.
Figure 23:
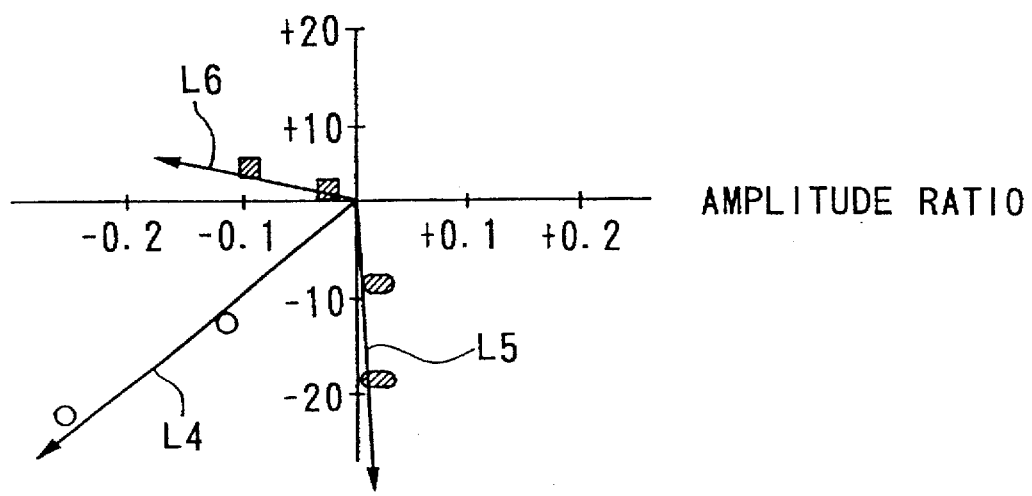
FIG. 23 is a diagram showing the change in the amplitude and phase of the third degree harmonic wave of a pulse wave due to medication delivery.

In order to put this detection method into practice, the present applicant obtained the diagrams in FIGS. 22 and 23 as clinical data. These diagrams show the types of changes in the phase and amplitude of the pulse wave spectra due to the delivery of medication; specifically, FIG. 22 shows the case for the second harmonics, and FIG. 23 shows the case for the third degree harmonics. In the respective diagrams, the vertical axis represents the phase change in each harmonic wave due to the medication delivery, and the horizontal axis represents the change in the ratio between the amplitude of the fundamental wave and the harmonic wave. Also, the respective plots connected by the lines L1 and L4 show the case in which nifedipine is given, the respective plots connected by the lines L2 and L5 show the case in which phentolamine is given, and the respective plots connected by the lines L3 and L6 show the case in which propranolol is given. As shown in FIG. 22, regarding the second harmonic waves, the delivery of nifedipine results in a delay in the phase and an increase in amplitude, while the delivery of propranolol results in a phase delay and a decrease in amplitude, and the delivery of phentolamine results in an advance in phase and an increase in amplitude. Additionally, as shown in FIG. 23, regarding the third degree harmonics, the delivery of nifedipine results in a phase delay and a decrease in amplitude, while the delivery of propranolol results in a decrease in amplitude, and the delivery of phentolamine results in a phase delay. Furthermore, it is apparent that the amount of change in the phase and amplitude depends upon the amount of medication given.

For this modification example, the data given in FIGS. 22 and 23 are used in medication delivery control. That is, for the present example, the occurrence of the condition requiring the delivery of medication is determined by detecting phase delays or amplitude changes in the second harmonic waves of the patient's pulse waves, and thus the necessary delivery of medication is performed.

10) In the above embodiments, it is determined whether or not to deliver medication based on the pulse waves taken from the patient, and if necessary the delivery of medication is performed automatically. However, the present invention is not limited to performing the delivery of medication automatically in this fashion. For example, it is possible to remove such medication delivery means as the micropump in the above embodiments, and to construct a pulse wave detection apparatus which can display or output the changes in the ratio between the fundamental spectrum and the harmonic spectra and the phase of the harmonic spectra of the pulse waves taken from the patient in a manner as shown, for example, in FIGS. 1, 2, 22, or 23. In this case, a doctor can make the determination of whether or not to deliver medication based on the results of the display or output from the pulse wave detection apparatus.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A medication delivery control apparatus, comprising:
   pulse wave detection means for obtaining pulse waves from a patient at predetermined regular time intervals;
   pulse wave analysis means for determining waveform parameters of the pulse waves; and
   medication delivery control means for causing delivery of medication if the waveform parameters meet preset conditions.

2. The medication delivery control apparatus of claim 1, further comprising means for measuring the blood pressure of the patient; and wherein said medication delivery control means causes the delivery of medication if the waveform parameters meet the preset conditions and the blood pressure is greater than a preset value.

3. The medication delivery control apparatus of claim 1, wherein said pulse wave analysis means includes means for determining the spectra of the pulse waves by applying a frequency analysis to the pulse waves and means for calculating the waveform parameters based on the spectra.

4. The medication delivery control apparatus of claim 3, wherein the waveform parameters are composed of amplitude ratios between respective harmonic spectra and fundamental spectra of the pulse waves.

5. The medication delivery control apparatus of claim 3, wherein the waveform parameters are composed of phase differences between respective harmonic spectra and fundamental spectra of the pulse waves.

6. The medication delivery control apparatus of claim 3, wherein the waveform parameters are composed of distortion of the pulse waves calculated from the spectra of the pulse wave.

7. A pulse wave detection apparatus, comprising:
   pulse wave detection means for detecting pulse waves from a patient; and
   pulse wave analysis means for determining waveform parameters of the pulse waves, and
   wherein said pulse wave analysis means includes means for determining the spectra of the pulse waves by applying a frequency analysis to the pulse waves and means for calculating the waveform parameters based on the spectra.

8. The pulse wave detection apparatus of claim 7, wherein the waveform parameters are composed of amplitude ratios between respective harmonic spectra and fundamental spectra of the pulse waves.

9. The pulse wave detection apparatus of claim 7, wherein the waveform parameters are composed of phase differences between respective harmonic spectra and fundamental spectra of the pulse waves.

* * * * *